US011304644B2

(12) United States Patent
Lu et al.

(10) Patent No.: US 11,304,644 B2
(45) Date of Patent: Apr. 19, 2022

(54) 3-D ELECTROPHYSIOLOGY HEART SIMULATION SYSTEM AND RELATED METHODS

(71) Applicant: Biosense Webster (Israel) Ltd., Yokneam (IL)

(72) Inventors: Albert Lu, Shanghai (CN); Guoqiang Wu, Beijing (CN); Weiguo Lai, Wuhan (CN)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 484 days.

(21) Appl. No.: 15/633,224

(22) Filed: Jun. 26, 2017

(65) Prior Publication Data

US 2018/0256056 A1 Sep. 13, 2018

Related U.S. Application Data

(60) Provisional application No. 62/468,283, filed on Mar. 7, 2017.

(51) Int. Cl.
*A61B 5/0402* (2006.01)
*A61B 5/044* (2006.01)
(Continued)

(52) U.S. Cl.
CPC .............. *A61B 5/327* (2021.01); *A61B 5/319* (2021.01); *A61B 5/339* (2021.01); *A61N 1/08* (2013.01);
(Continued)

(58) Field of Classification Search
CPC . A61B 5/04028; A61B 5/044; A61B 5/04021; A61B 2576/023; A61B 34/10
See application file for complete search history.

(56) References Cited

U.S. PATENT DOCUMENTS 6,226,542 B1 5/2001 Reisfeld
6,892,091 B1 5/2005 Ben-Haim et al.
(Continued)

FOREIGN PATENT DOCUMENTS

EP 2 047 797 A2 4/2009

OTHER PUBLICATIONS

EPO European Search Report for EP Application No. 18160136.0, dated Jun. 5, 2018, 11 pages.
(Continued)

*Primary Examiner* — Jonathan Cwern
*Assistant Examiner* — Amal Aly Farag
(74) *Attorney, Agent, or Firm* — Lewis Roca Rothgerber Christie LLP

(57) ABSTRACT

A system for simulating a medical procedure includes: a physical model of an organ including a sensor mesh; directed at the physical model; a user input device including a distal end inserted within the physical model; a display device; and a simulation controller coupled to the sensor mesh, the camera system, the user input device, and the display device, the simulation controller including a processor and memory storing instructions to cause the processor to: initialize a simulation of the organ; display, on the display device, a state of the simulation; compute a location of the distal end within the physical model of the organ based on contact data from the sensor mesh and images received from the cameras; receive user input from the user input device; update the state of the simulation of the organ in accordance with the user input; and display the updated state of the simulation.

19 Claims, 12 Drawing Sheets
(2 of 12 Drawing Sheet(s) Filed in Color)

(51) Int. Cl.
*A61B 5/327* (2021.01)
*A61N 1/08* (2006.01)
*A61B 5/319* (2021.01)
*A61B 5/339* (2021.01)
*A61B 18/00* (2006.01)
*A61B 5/00* (2006.01)

(52) U.S. Cl.
CPC ..... *A61B 5/742* (2013.01); *A61B 2018/00351* (2013.01); *A61B 2576/023* (2013.01)

(56) References Cited

U.S. PATENT DOCUMENTS

| | | | |
|---|---|---|---|
| 7,536,218 B2 | 5/2009 | Govari et al. | |
| 8,357,152 B2 | 1/2013 | Govari et al. | |
| 8,478,383 B2 | 7/2013 | Bar-Tal et al. | |
| 9,662,033 B2 | 5/2017 | Severino | |
| 2004/0126746 A1 | 7/2004 | Toly | |
| 2007/0106146 A1* | 5/2007 | Altmann | A61B 5/0035 |
| | | | 600/407 |
| 2008/0161796 A1* | 7/2008 | Cao | A61B 18/1492 |
| | | | 606/41 |
| 2011/0130648 A1 | 6/2011 | Beeckler et al. | |
| 2012/0082969 A1* | 4/2012 | Schwartz | G09B 23/285 |
| | | | 434/262 |
| 2012/0283590 A1* | 11/2012 | Afonso | A61B 5/04012 |
| | | | 600/523 |
| 2013/0010081 A1* | 1/2013 | Tenney | A61B 34/30 |
| | | | 348/47 |
| 2013/0274582 A1* | 10/2013 | Afonso | A61B 5/0044 |
| | | | 600/374 |
| 2013/0330701 A1* | 12/2013 | Rubinstein | G09B 23/285 |
| | | | 434/272 |
| 2015/0105770 A1* | 4/2015 | Amit | A61B 18/1492 |
| | | | 606/41 |
| 2016/0183824 A1 | 6/2016 | Severino | |
| 2016/0331262 A1* | 11/2016 | Kuck | A61B 5/04085 |
| 2017/0185740 A1* | 6/2017 | Seegerer | G06F 30/20 |
| 2019/0254555 A1* | 8/2019 | Bouchard | G01K 7/16 |
| 2021/0184863 A1 | 6/2021 | Shahin | |

OTHER PUBLICATIONS

European Examination Report for corresponding EPA No. 19164729.6 dated Jul. 9, 2020.
European Examination Report for corresponding EPA No. 191647296 dated Mar. 9, 2021.
Martin K. Stiles et al., "the Effect of Electrogram Duration on Quantification of Complex Fractionated Atrial Electrograms and Dominant Frequency", Journal of Cardiovascular Electrophysiology, vol. 19, No. 3, Mar. 1, 2008, pp. 252-258.

* cited by examiner

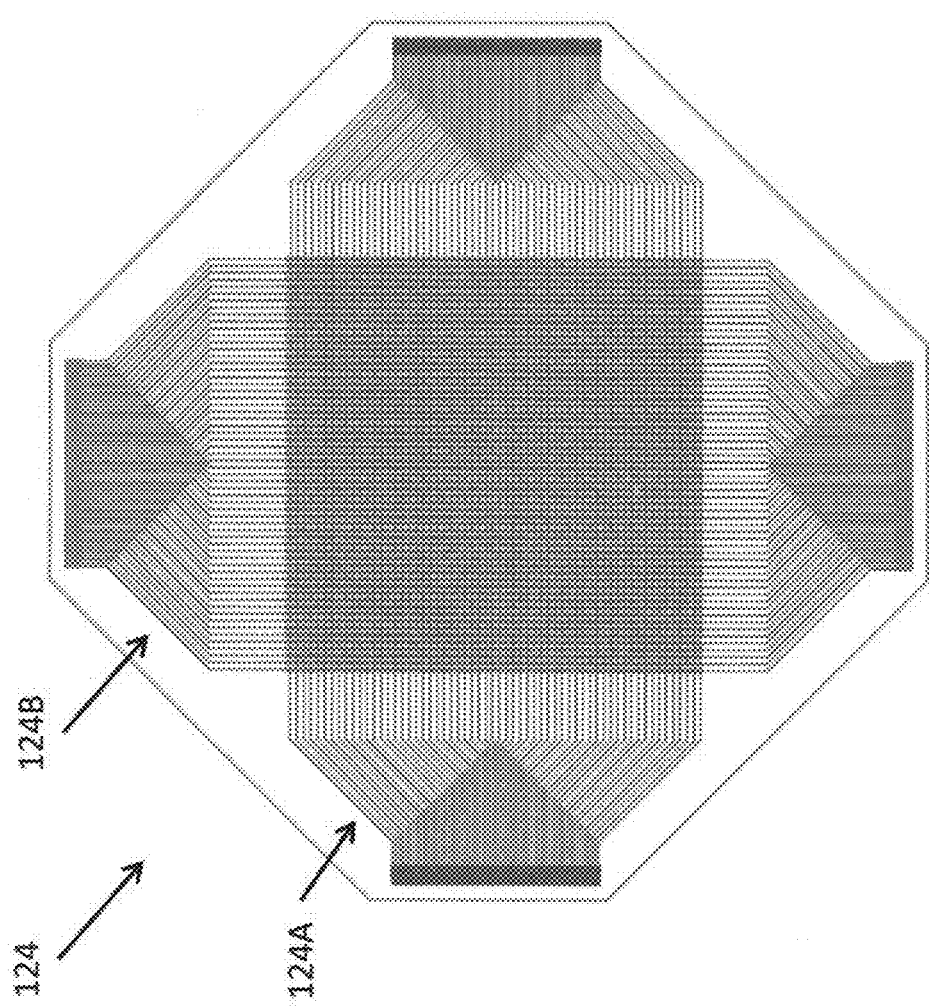

3-D ELECTROPHYSIOLOGY HEART SIMULATION SYSTEM AND RELATED METHODS

CROSS-REFERENCE TO RELATED APPLICATION(S)

This application claims the benefit of U.S. Provisional Patent Application No. 62/468,283, filed in the United States Patent and Trademark Office on Mar. 7, 2017, the entire disclosure of which is incorporated by reference herein.

FIELD OF INVENTION

Aspects of embodiments of the present invention generally relate to methods and devices to simulate performing invasive medical treatments, in particular, a physical model of a heart and a system for simulating the electrophysiological behavior of a heart during a medical procedure.

BACKGROUND

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Accordingly, numerous procedures for treating cardiac arrhythmias have been developed, including catheter ablation procedures.

As shown in FIG. 1A, a known catheter-based electrophysiology mapping and ablation system 10 provides a diagnostic 3-D electroanatomical map 20 of a heart 12 of a patient 22 which visualization may include visualization of the real-time calculated position and orientation of a catheter or probe 14 within the patient's heart. The system also enables energization of electrodes on the catheter for therapeutically ablating selected heart tissue. The system has been developed to provide multiple functions, including (1) to clearly define the endocardial anatomy as a 3-D representation or anatomical map 20 for display on a first display 27, (2) to record and catalog sampled electrograms 21 for display on a second display 11, (3) to display the activation sequence (or other data) compiled from recorded electrograms 21 in representative visual indicia or imagery superimposed on the 3-D anatomical map 20 to render it into a 3-D electroanatomical map for display on the first display 27, (4) to track in real-time the current location of electrode catheter in the heart, and (5) to record precise locations of sites of interest such as places where RF energy has been applied. In some embodiments, the system displays the current location of the catheter in the heart by projecting accurate representations of them into the 3-D representation 20 of the heart, and also displays with the 3D representation 20 the places where RF energy has been applied to indicate the locations of lesions resulting from ablation. As such, the system provides various benefits, including, e.g., minimizing radiation exposure during fluoroscopy, increasing the accuracy of targeted RF ablation and reacquisition of pacing sites for re-ablation. Such a system is disclosed in U.S. Application Ser. No. 14/587,964, filed Dec. 31, 2014, titled SYSTEM AND METHOD FOR VISUALIZING ELECTROPHYSIOLOGY DATA, now U.S. Pat. No. 9,662,033, the entire disclosure of which is incorporated herein by reference.

In a two-step procedure—mapping followed by ablation—a catheter containing one or more electrical sensors is advanced into the heart to acquire position (e.g., location and orientation) and electrophysiological data at a multiplicity of locations for generating the 3-D electroanatomical map. These data are then utilized to select target areas at which ablation is to be performed by energizing the catheter electrodes placed in contact with the target areas. The ablation process forms non-conducting lesions which destroy the unwanted electrical pathways.

The system 10 is managed by a system controller or console 30, including a processing unit 32 communicating with a memory 34, wherein is stored software for operation of system 10. In some embodiments, the controller 30 is a computer including a processing unit 32 and is typically managed by operator 24 who sets parameters of system 10. In some embodiments, the system 10 includes an RF ablation module 50 and the controller 30 includes a position module 54 to determine the location and orientation of the catheter distal tip. In some embodiments, the system 10 also includes a force sensing module 55 to determine a force applied to the catheter distal tip such as when the distal tip comes into contact with tissue surface. The processing unit 32 uses the RF ablation module 50 to monitor and control ablation parameters such as the level of ablation power applied via the electrodes on the catheter. The monitoring may be implemented by any suitable tracking method known in the art.

To display on the 3-D map on the first display 27 the activation sequence (or other data) compiled from recorded intracardiac electrograms 21 sensed by the catheter, the 3-D map 20 includes electrical activation maps which are superimposed on the 3-D anatomical map to render the 3-D electroanatomical map 20. Such maps are color-coded to reveal electrical activation sequence which can reveal regions or locations with abnormal electrical activity. For simpler arrhythmias, the operator may merely refer to the electrograms 21 displayed on the second display 11, but for more complex arrhythmias, the 3-D electroanatomical map 20 provides a handy and useful visual representation readily revealing the heart anatomy and electrical propagation in the heart tissue. As shown in FIG. 2, the 3-D electroanatomical map 20 includes a 3-D anatomical map with superimposed imagery representing local activation times (LATs) which are color-coded to indicate for a location in the heart the interval between the beginning of the local electrogram of the mapping catheter and the reference signal, with red representing the earliest activation recorded and purple representing the latest activation recorded.

As shown in FIG. 3, FIG. 3A and FIG. 3B, the 3-D electroanatomical map 20 includes lesion-representative visual indicia representing the locations where ablation has occurred. Because lesions resulting from ablation block electrical pathways, the color-coded LATs shown in the 3-D electroanatomical map 20 acquired during or subsequent to an ablation session indicate whether the lesions were appropriately positioned and have successfully formed a successful block, or whether further ablation is needed to form additional lesions. Although the electrograms 21 on the second display 11 may be used during or subsequent to an ablation session, the 3-D map 20 on the first display 27 is handy and useful especially where a more complex arrhythmia is involved.

The electrical activation maps, anatomic positional information, i.e., of the distal portion of the catheter, and other functional images are prepared by the console and its modules, according to the methods disclosed in U.S. Pat. Nos. 6,226,542, and 6,301,496, and in commonly assigned U.S. Pat. No. 6,892,091, whose entire disclosures are herein incorporated by reference. Commercial products embodying elements of the system are the CARTO, CARTO XP, and/or CARTO® 3 Systems, available from Biosense Webster, Inc., Irwindale, Calif. 91765, which performs catheter localization (of position and orientation) and produces 3-D electroanatomical maps of the heart as required.

Areas determined to be abnormal, for example by evaluation of electrical activation maps, can be targeted and ablated by application of thermal energy, e.g., by passage of radiofrequency electrical current from a radiofrequency (RF) generator of the RF ablation module 50 through a cable 37 providing current to the catheter 14, including one or more ablation electrodes 17A at or near the distal tip 15, as shown in FIG. 1B, which apply the radiofrequency energy to the target tissue. Pacing signals and other control signals may also be conveyed from the console 30 through the cable 37 and the catheter electrode(s) to the heart 12. Moreover, electrical signals (for example, intracardiac electrocardiography or ECG signals) are conveyed from the heart 12 to the console 30 via the catheter electrodes 17A and/or 17B.

In some embodiments of the system 10, ECG body surface patches, including at least patches 38 are affixed to the patient's body. While the catheter electrodes 17A are sensing intracardiac ECG signals, a plurality of electrodes in the ECG body surface patches 38 measure ECG signals across the heart and torso to provide reference signals for the intracardiac ECG signals measured by the catheter electrodes 17A and/or 17B which are displayed on the second display 11. However, embodiments of the present invention are not limited thereto and may be performed without the use of ECG body surface patches.

As part of the catheter localization capabilities of the console 30, according to one embodiment of the present invention, a non-homogenous magnetic field is generated around the patient 22, for example, by a location pad containing magnetic field generator coils 28 that is placed under the patient. The magnetic fields generated by coils 28 generate electrical signals in orthogonal coils $C_x$, $C_y$, $C_z$ (see FIG. 1B) of an electromagnetic (EM) sensor located in the distal tip 15 of catheter 14 (see FIG. 1C). The electrical signals are conveyed to the console 30 for the position module 54 to analyze the signals so as to determine the position (location and orientation) of the catheter.

As also part of the catheter localization capabilities of the console, the catheter electrodes 17A and/or 17B are connected by lead wires (not shown) in the catheter 14 and the cable 37 to current and voltage measurement circuitry in the console 30. The console is also connected by wires and a patch unit 31 to the body surface electrodes 18, which may be any type of body electrodes known in the art, such as button electrodes, needle electrodes, subcutaneous probes, or patch electrodes. The body surface electrodes 18 are typically in galvanic contact with the body surface of the patient 13 and receive body surface currents therefrom. The body surface electrodes 18 may be adhesive skin patches generically referred to as active current location (ACL patches) and may be placed on the body surface of the patient 22 in the vicinity of the catheter 14. The console 30 includes voltage generators which are connected to the ACL patches 38 and which the processor 32 uses to calculate impedance of the patient tissue between the catheter electrodes 17A and 17B and the location of the patches 18. Accordingly, the console 30 uses both magnetic-based position sensing and impedance-based measurements to determine catheter location, as described in U.S. Pat. No. 7,536,218, issued to Govari et al., and U.S. Pat. No. 8,478,383, issued to Bar-Tal et al., the entire content of both of which are herein incorporated by reference.

In some embodiments, impedance measurements are also used by the console 30 in detecting contact between the catheter distal tip 15 and tissue of the heart 12, for example, in detecting a change in impedance when the distal tip 15 is in contact with blood versus tissue. In some embodiments, the catheter includes a force sensor 60, as shown in FIG. 1B, to detect contact between the catheter distal tip and tissue of the heart. Aspects of a force sensor are described in U.S. Pat. No. 8,357,152, issued on Jan. 22, 2013 to Govari et al., entitled CATHETER WITH PRESSURE SENSING, and in U.S. Patent Publication No. 2011/0130648, to Beeckler et al., filed Nov. 30, 2009, entitled CATHETER WITH PRESSURE MEASURING TIP, both of whose disclosures are incorporated herein by reference.

With reference to FIG. 1B, the force sensor 60 includes a resilient coupling member 61, which forms a spring joint. In some embodiments, the coupling member 61 has hollow cylindrical form with a central lumen 62 and one or more helices 63 joint sensing assembly are divided between two subassemblies on opposite sides of the spring joint. One subassembly comprises the coil 82 distal of the spring joint, which is driven by a current provided to the catheter via cable 37 to generate a magnetic field. This field interacts with a second subassembly, comprising the coils 76, 78 and 80, which are located proximal of the spring joint. In some embodiments, the coil 80 and the coil $C_z$ are one and the same.

The coils 76, 78 and 80 are fixed at the same proximal distance from the coil 82 but at different radial locations. In the illustrated embodiment, the three coils are spaced azimuthally 120 degrees apart at the same axial distance from the coil 82 along the longitudinal axis 84. The coils 76, 78 and 80 generate electrical signals in response to the magnetic field transmitted by coil 82. These signals are processed by the force sensor module 55 in order, for example, to measure the axial displacement of spring joint along a longitudinal axis 84 of the distal tip 15, as well as to measure the angular deflection of the spring joint from the longitudinal axis 84. From the measured displacement and deflection, the force sensor module 55 is able to evaluate, typically using a previously determined calibration table, a magnitude and a direction of the force on the spring joint, including axial displacement of the distal section 15 when it is in contact with the tissue.

As noted above, the catheter 14 is coupled (or connected) to the console 30, which enables the operator 24 to observe and regulate the functions of the catheter 14. The processor 32 and/or the console 30 include appropriate signal processing circuits coupled to drive the display 27 to display visual imagery including the 3-D electroanatomical map 20 along with a superimposed visual indicia of a catheter representing the location and orientation of at least the distal tip 15 of the catheter.

A typical diagnostic mapping procedure may involve an operator placing the catheter distal tip (which carries the EM sensor with coils Cx, Cy and Cz, impedance-sensing catheter electrodes 17A and/or 17B, and/or the force sensor 60) in contact with tissue in a chamber of interest in the patient's heart at multiple locations. At each of these locations, the mapping and ablation system 10 systematically acquires via the catheter data on the location and the local electrogram at that location. Through these sequential acquisitions, a 3-D anatomical map is created by the system 10 in real-time, with visual indicia of electrophysiological data, e.g., LATs, superimposed on the 3-D anatomical map to form the 3-D electroanatomical map 20 that is displayed on the display 27. Location data of the catheter is also used by the console 30 to provide visual indicia representative of the position of the catheter that is superimposed on the 3-D electroanatomical map 20.

A typical therapeutic ablation procedure may involve an operator studying the 3-D electroanatomical map 20 on the display 27 and/or the ECGs on the display 11 and recognizing abnormalities or defective electrical impulses indicative of an arrhythmia in the chamber of interest. Upon the operator identifying the source or origin of the abnormal electrical impulses in the heart or adjacent regions, such as the pulmonary veins, the operator places the same or another catheter in contact with heart tissue at selected locations to ablate the tissue at these locations in forming lesions to block, contain, isolate or otherwise stop the abnormal electrical impulses. Location data of the catheter may also be used by the console 30 to provide visual indicia representative of ablation/lesion locations that are superimposed on the 3-D electroanatomical map 20.

As the operator is ablating, the operator may refer to the electroanatomical map 20 on the first display 27 and/or the ECGs on the second display 11, which are refreshed in real-time, so as to assess the effect the lesions have on the abnormal electrical impulses and thus the progress of the ablation procedure. For example, an errant electrical impulse in the right atrium which arises in a pulmonary vein may require a circumferential block at the ostium of the pulmonary vein to successfully treat the arrhythmia. As such, the operator continues to ablate the circumference of the ostium until the 3-D electroanatomical map on the first display 27 and/or the ECGs on the second display 11 show a complete block of the errant electrical impulses from entering the left atrium from the pulmonary vein.

Mapping and ablating in the heart pose special challenges due to the size of the heart and its chambers, ostia and tubular regions. Manipulating the catheter is a high-skill task and the success of catheter-based mapping and ablation procedures depends in a large part on proper manipulation and placement of the catheter which typically require hands-on training with an actual catheter to learn the touch and feel of maneuvering the catheter within a small chamber having surface formations and configurations resembling a heart. Moreover, ablation with the catheter involves the judgment of a health care professional to properly interpret the real-time electroanatomical maps and/or ECGs to determine the effect of the ablation on the electrical propagation pathways through the heart. Various patients may react differently to the treatment, based on the particular nature of their conditions. As such, the health care professional must be able to recognize and distinguish between different circumstances and patterns.

Generally, cardiac electrophysiologists are trained to perform catheter-based mapping and ablation procedure with a combination of classroom teaching and hands-on training using animals and passive systems and devices that provide neither simulation nor accurate simulation of signals and readings that would be provided by an electrophysiology mapping and ablation system during a procedure with a patient.

SUMMARY

The present invention recognizes the benefits of training electrophysiologists with the use of a conventional EP catheter, a conventional electro-anatomical mapping and ablation system, and a 3-D heart model that resembles an actual heart in terms of shape and size so as to provide training in various aspects, including, the "feel" and the handling and manipulation of a catheter within a patient's heart, and the reading of normal and defective ECGs during EP procedures, including electroanatomical mapping and ablation procedures. In some embodiments, a simulation system for use with a conventional EP catheter and a conventional electro-anatomical mapping and ablation system, for example, the CARTO, CARTO XP or CARTO 3, includes a simulation controller in communication with the mapping and ablation system, and a sensor mesh of the 3-D heart model that in responsive to one or more activities of and/or interacts with the catheter, including., e.g., surface contact by the catheter, emitting electrical impulses for sensing by the catheter, such as for mapping and/or ablation, wherein the simulation controller is responsive to such activities and/or interactions in providing control and display signals to the mapping and ablation system, including its one or more displays, to respond and react in a manner that simulates responses, reactions and functions of the mapping and ablation system to such activities during a mapping and/or ablation procedure in a heart of an actual patient, including the generation of graphic representations of a 3-D anatomical map, a 3-D electroanatomical map, visualization of catheter location (including position and orientation) and/or electrograms.

In some embodiments, the 3-D heart model includes a right atrium and the simulation controller includes a memory with instructions providing signals representative of normal ECGs of the right atrium and defective ECGs (arrhythmias) of the right atrium, including, e.g., atrial flutter and atrial fibrillation, for display on a display of the mapping and ablation system, in simulating the right atrium of a patient's heart and corresponding arrhythmias. In some embodiments, the 3-D heart model includes a right ventricle and the simulation controller includes a memory with instructions providing signals representative of normal ECGs of the right ventricle and defective ECGs (arrhythmias) of the right ventricle, including, e.g., ventricular tachycardia, for display on a display of the mapping and ablation system, in simulating the right ventricle of a patient's heart and corresponding arrhythmias.

In some embodiments, the simulation controller is configured to receive and process signals representative of catheter contact locations in the 3-D heart model as collected or acquired by the sensor mesh and/or a position sensor in the catheter in response to movement and contact of the catheter in the 3-D heart model, and provide to the mapping and ablation system control and display signals representative of ECGs evolving in real-time in response to the catheter contact locations, in simulating a patient's heart and corresponding arrhythmias before, during and after a mapping and ablation procedure. In some embodiments, the simulation controller is configured to provide to the mapping and ablation system control and display signals representative of normal ECGs in simulating a successful ablation procedure, where the catheter contact locations are representative of a proper ablation block or isolation for treating a selected arrhythmia.

Aspects of embodiments of the present invention relate to a system and method for providing simulations of invasive medical treatments, such as performing ablation of myocardial tissue as treatment for cardiac arrhythmias. While various embodiments of the present invention will be described below with respect to ablation of myocardial tissue, embodiments of the present invention are not limited thereto and may be applied to simulate different types of treatments to different types of tissue.

According to some embodiments of the present invention, a system for simulating a medical procedure includes a physical model of an organ (or tissue of organ) including a sensor mesh; a camera system including a plurality of cameras having overlapping fields of view directed at the physical model of the organ; a user input device including a distal end inserted within the physical model of the organ; a display device; and a simulation controller coupled to the sensor mesh, the camera system, the user input device, and the display device, the simulation controller including a processor and memory, the memory storing instructions that, when executed by the processor, cause the processor to: initialize a simulation of the organ; display, on the display device, a representation of a state of the simulation of the organ; receive contact data from the sensor mesh; receive images from the cameras; compute a location of the distal end of the user input device within the physical model of the organ in accordance with the contact data and the images; receive user input from the user input device; update the state of the simulation of the organ in accordance with the user input; and display, on the display device, the updated state of the simulation.

The organ (or tissue of organ) may be a heart (or heart tissue).

The displayed state of the simulation may include an electroanatomical map of the heart.

The displayed state of the simulation may include one or more electrograms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6A is an illustration of a sensor mesh according to one embodiment of the present invention.

DETAILED DESCRIPTION

Aspects of the present invention are directed to a system for simulating catheter-based mapping and ablation, where the system provides a physical 3-D model of an organ, such as a heart, which simulates the behavior of the organ, including normal and abnormal electrical activities, and its responses to surface contact during mapping and ablation by a catheter, in various scenarios, as sensed, measured by the catheter and represented by a 3-D electroanatomical map generated by a conventional electrophysiology mapping and ablation system, such as the CARTO, CARTO XP and CARTO® 3 System, available from Biosense Webster, Inc. of Irwindale, Calif. The simulation system may be used for demonstrating and training health care professionals, including cardiac electrophysiologists, in the use of the conventional electrophysiology mapping and ablation systems. Compared to conventional systems for training, simulation systems according to embodiments of the present invention provide users with a physical experience of handling and manipulating a catheter within the confines of a 3-D model that physically resembles an organ, such as a heart, in terms of shape and size, and a simulated output that more accurately corresponds to what would be experienced by a health care professional performing a mapping and/or ablation procedure on a patient.

Figure 1A:
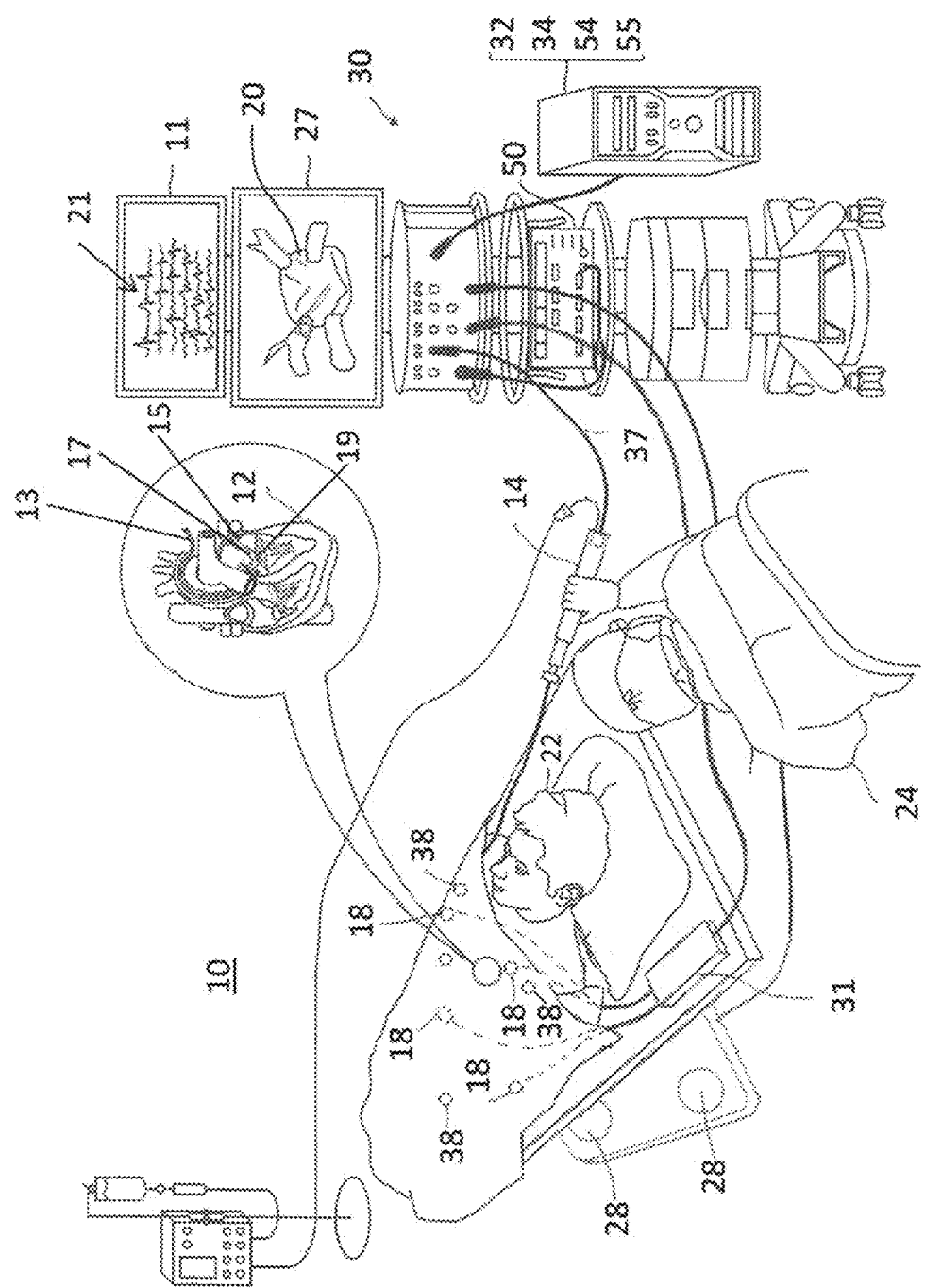
FIG. 1A is a schematic, pictorial illustration of a known catheter-based electrophysiology mapping and ablation system.
Figure 4:
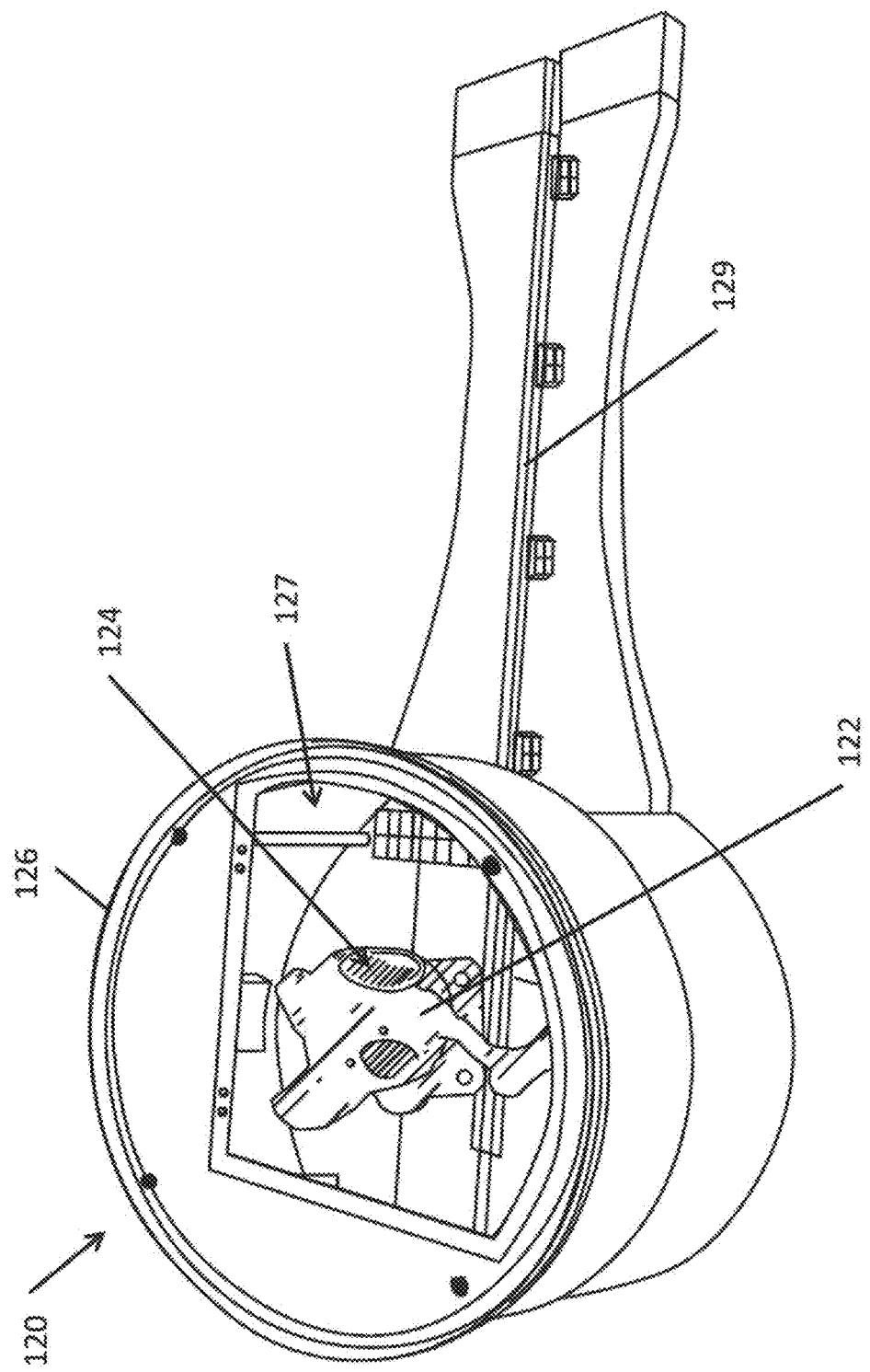
FIG. 4 depicts a portion of simulation system according to one embodiment of the present invention.
Figure 5:
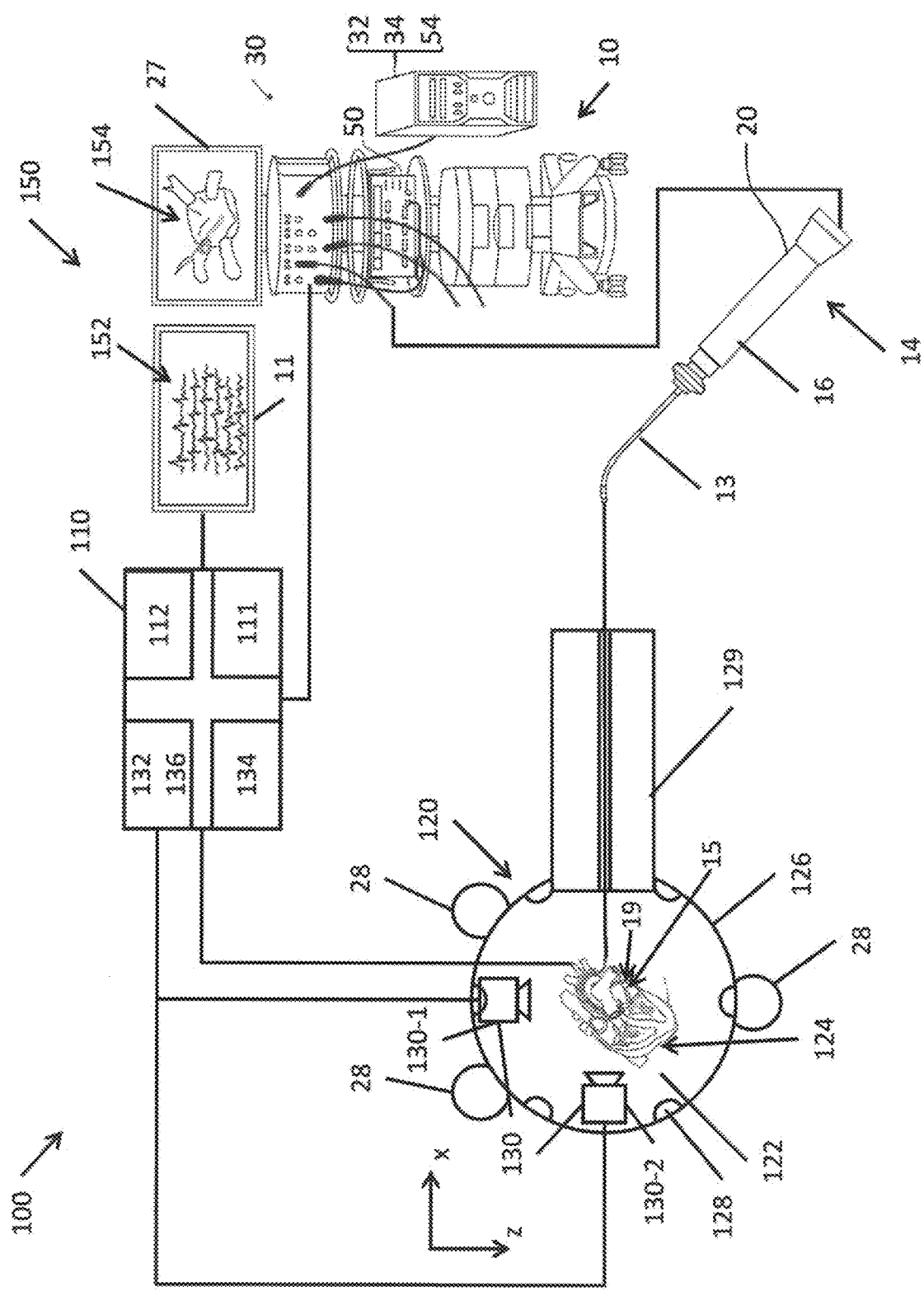
FIG. 5 is a block diagram a simulation system according to one embodiment of the present invention.

FIG. 4 depicts a portion of simulation system 100 according to one embodiment of the present invention. FIG. 5 is a block diagram of the simulation system 100 according to one embodiment of the present invention. The simulation system 100 may be used to simulate portions or all of the system 10 shown in FIG. 1A from the perspective of the operator 24.

As shown in FIG. 5, the simulation system 100 includes a simulation controller 110 configured to receive inputs from and provide outputs to various portions of the simulation system 100, to perform a computer simulation of a human heart, and to generate a simulation output. In some embodiments, the simulation system 100 is used in conjunction with a catheter-based electrophysiology mapping and ablation system 10, such as the CARTO® 3 system described above. The simulation controller 110 may include a computer processor 111 and a memory 112 storing program instructions that are executed by the processor to perform the functions of simulating a catheter-based mapping and/or ablation procedure. The simulation controller 110 may also include various input/output controllers (e.g., universal serial bus or USB controllers, amplifiers, analog-to-digital converters, and digital-to-analog converters) to receive the inputs from the various portions of the simulation system 100 and to control peripheral devices, and a display controller to output display signals to one or more display devices (e.g., a television, a computer monitor, or virtual reality goggles).

The simulation system 100 further includes a three-dimensional heart model system 120 that includes an anatomically accurate physical model of a heart 122, or one or more portions thereof. The physical model of the heart 122 is a three-dimensional physical device that is the size and shape of a human heart. In various embodiments of the present invention, the physical model 122 may have a variety of different sizes and shapes, corresponding to the variety of different sizes and shapes of human hearts that may be encountered by professional cardiac electrophysiologist. In some embodiments, the physical model 122 corresponds to an anatomically accurate model of all or fewer than all of the four chambers of a human heart (e.g., left atrium, right atrium, left ventricle, right ventricle, or combinations thereof). For example, the physical model 122 may be a model of only the left atrium of the heart. The physical model 122 may be constructed using any of variety of techniques, such as injection molding and three-dimensional printing. The physical model 122 may be formed of a material that is similar to living heart tissue (e.g., in terms of deformability and elasticity). The inner surfaces of the physical model 122 are lined with a sensor mesh 124 that is coupled to the simulation controller 110. In some embodiments, the sensor mesh 124 is embedded within the physical model 122. The physical model 122 may be surrounded by an enclosure 126. In some embodiments, the enclosure has an opaque surrounding wall serving as a visual blind occluding direct viewing of the heart model by the operator (or trainee), and may include an opening 127 that is adapted to receive an opaque cover or a transparent window whose viewing area size is adjustable.

In some embodiments, a camera system 130 is used to image the physical model 122. The camera system 130 may include a plurality of cameras (e.g., two cameras). The cameras may be digital cameras that include an image sensor such as a charge coupled device (CCD) or a complementary metal oxide semiconductor (CMOS) sensor. In some embodiments, light sources 128 are inside or near the enclosure 126 to illuminate the physical model 122 and its interior. In embodiments that include a camera system 130, the physical model 122 may be formed of a transparent material such that the cameras can image the interior of the physical model 122. Imaging the interior of the physical model 122 may, in some circumstances, be easier in embodiments where the physical model 122 corresponds to fewer than all of the four chambers of the heart, because there may be fewer layers of transparent material potentially obscuring the locations of interest (e.g., the catheter tip). The camera system 130 may be controlled by a camera module control system 132 and the light sources 128 may be controlled by a light source control system 134, as shown in FIG. 5. In some embodiments, the camera module control system 132 and the light source control system 134 are integrated into the simulation controller 110, as shown in FIG. 5. The images captured by the camera system 130 may be processed by a video collection and processing system 136, which, in some embodiments, is integrated into the simulation controller 110.

Figure 1B:
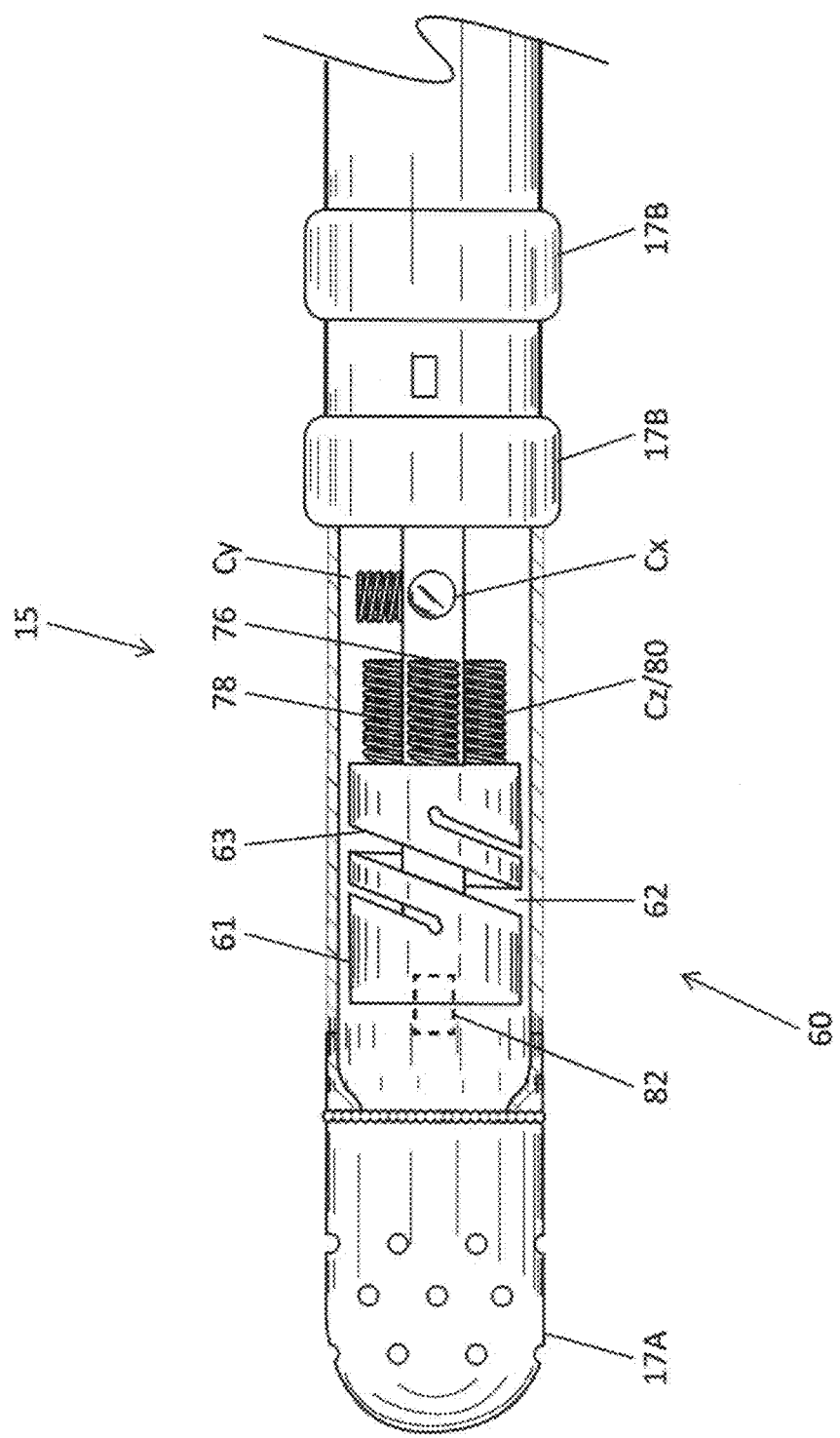
FIG. 1B is a side-elevational view of a catheter distal tip, with part(s) removed to show details, according to one embodiment.
Figure 1C:
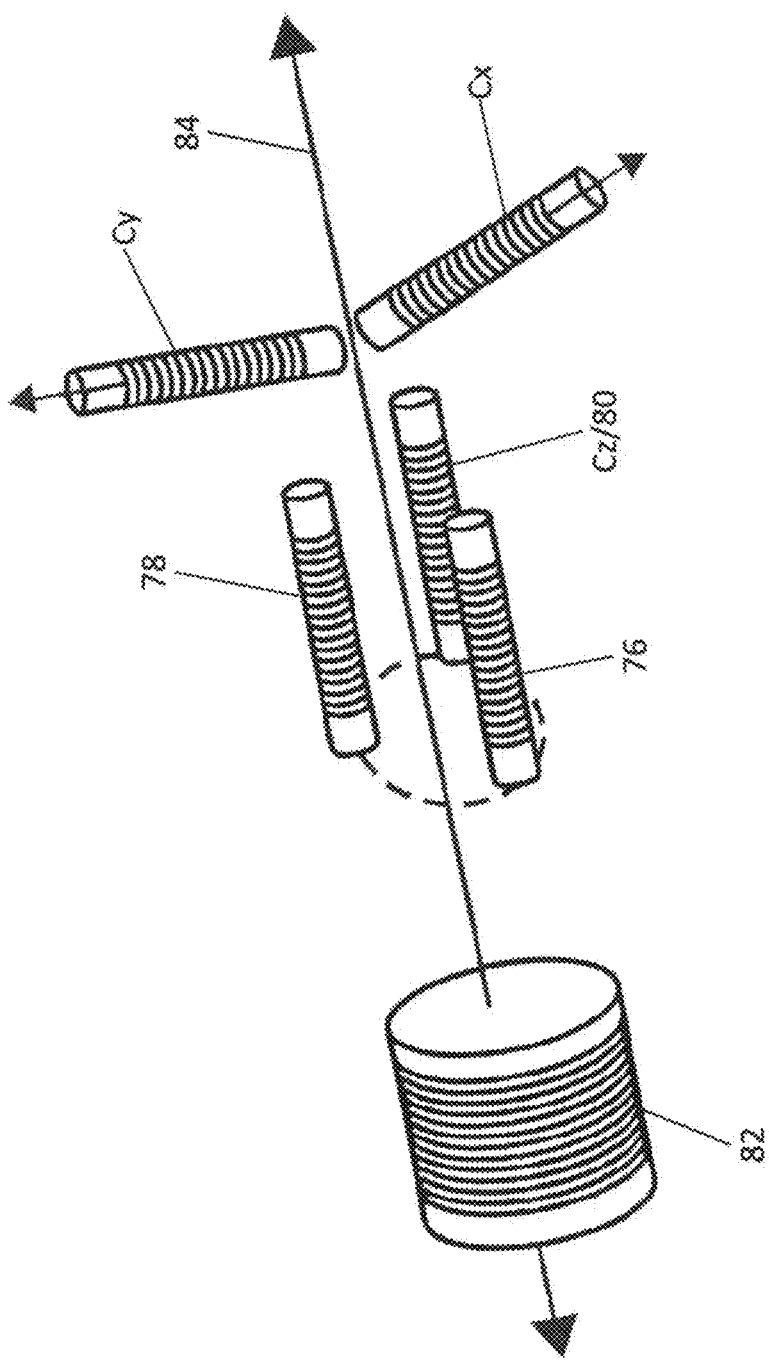
FIG. 1C is a schematic representation of coil components of a force sensor and a position sensor of the catheter distal tip of FIG. 1B.
Figure 2:
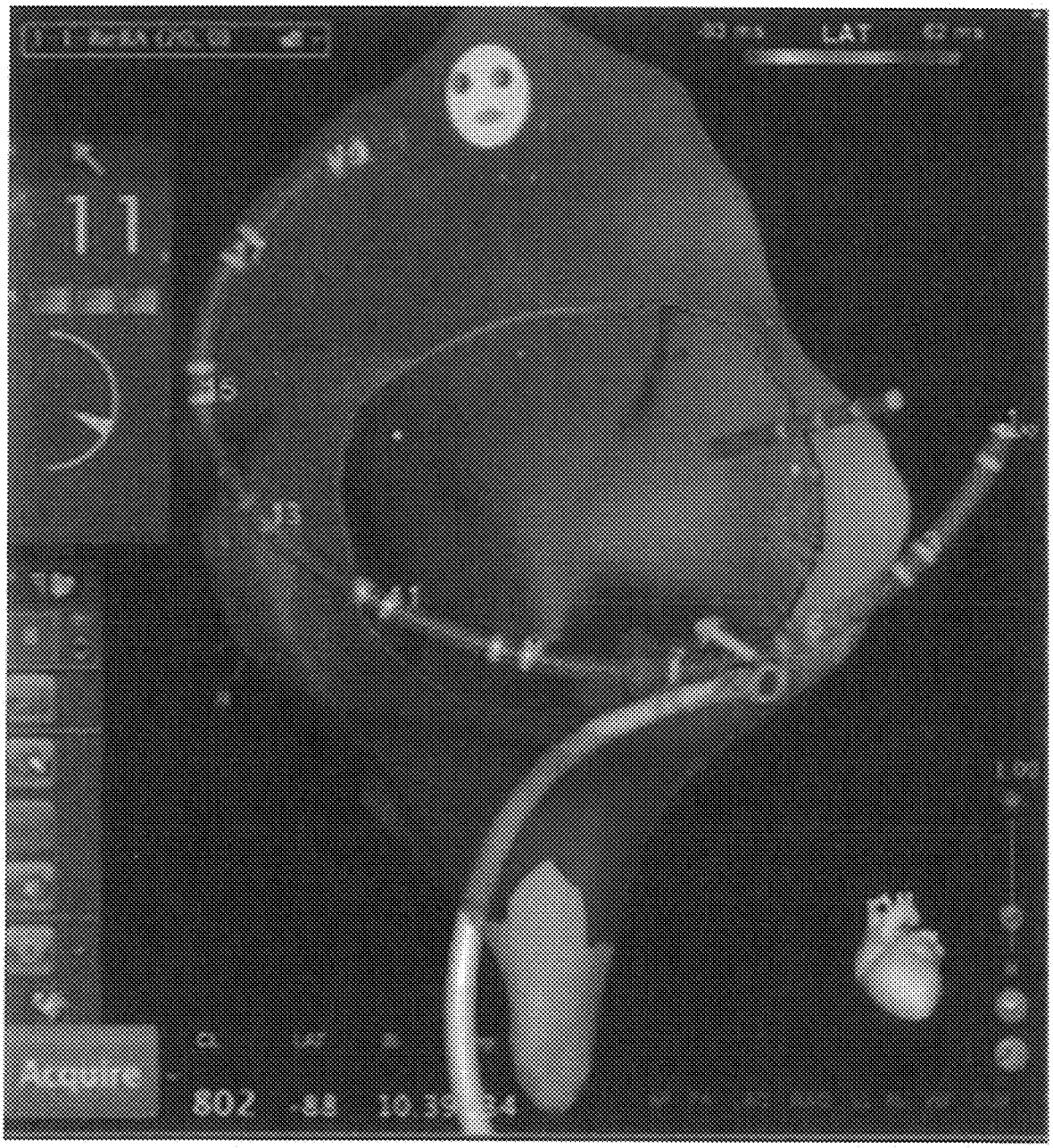
FIG. 2 is sample color-coded LAT map generated by the system of FIG. 1A, based on acquisitions by electrodes carried on catheter probes which are also visually represented in the map. Color red shows earliest depolarization, followed by orange, yellow, green, and blue, with purple showing latest depolarization.

As shown in FIG. 5, the simulation system 100 may be used in conjunction with a catheter-based electrophysiology mapping and ablation (EMA) system 10, such as the CARTO® 3 system described above with respect to FIG. 1A. For example, the three-dimensional heart model system 120 may be placed within the radiation field, including, e.g., on top, of a location pad including magnetic field generator coils 28, which are coupled to the system controller 30 of the EMA system 10 (e.g., the three-dimensional heart model system 120 may be placed on a surgical table configured to work with the EMA system 10). In this way, the physical heart model 122 may be located in approximately the same position with respect to the magnetic field generator coils 28 as a patient's heart would be during an actual procedure. The catheter 14 of the EMA system 10 (or a modified version thereof) may act as a user input device 14 for the user of the simulation system 100. The catheter 14 may include a control handle 16, an elongated catheter body 13, a deflectable intermediate section 19, and a distal section 15, as better shown in FIG. 1A. In some embodiments, the catheter includes an EM sensor with coils Cx, Cy, Cz, impedance-sensing electrodes 17A and/or 17B and/or a force sensor 60 housed in a distal end portion of the catheter, as shown in FIG. 1B and FIG. 1C.

The three-dimensional heart model system 120 may further include a channel 129 for receiving the catheter body 13. The channel 129 supports and guides the catheter body 13 and may simulate the distance and path traveled by the catheter body 13 from the catheter control handle 16 to the heart during a cardiac mapping and/or ablation procedure performed on a patient in which the catheter is inserted and advanced through the vasculature, e.g., femoral artery, of the patient.

The simulation controller 110 runs a computer simulation of a human heart, and generates a simulation output. The simulation output may include simulated electrograms 152, which may be displayed on the second display device 11. The simulation output may also provide signals to the system controller 30 of the EMA system 10, where the simulation output may include information that simulates the signals, including intracardiac signals, that would be captured by the ECG body surface patches 38 that would be attached to an actual patient. In this way, the catheter and the EMA system 10 may be operated in a substantially unmodified manner to locate the tip of the catheter 14 as positioned by the operator within the physical heart model 122 based on interactions between the magnetic fields generated by the magnetic field generators 28 and EM sensor coils Cx, Cy and Cz and to generate an anatomical map 154 of the heart model 122 for viewing on the display 154, as shown in FIG. 5., by placing the catheter in contact with surface of a chamber of interest of the heart model at multiple locations, in the manner described hereinabove. For example, at each contact location, data is recorded, including at least position data corresponding to the position of contact. Through sequential acquisitions of multiple contact locations, a 3-D anatomical map is created in real-time based on collected position data. Where the data recorded includes simulated electrophysiological data, for example, local activation times (LATs), electrophysiological data can be superimposed on the anatomical map to create an electroanatomical map, including, for example, color-coding representing activation sequence and velocity of activation.

In some embodiments, the position data for rendering a 3-D anatomical map are generated by the coils Cx, Cy and Cz of the EM sensor interacting with the magnetic field generators 28 to generate signals that are processed by the position module. In some embodiments, where the 3-D heart model 122 is devoid of emitting eletrophysiological signals, and in the absence of impedance measurements that would otherwise be available from an actual patient's heart, the position module 54 relies on the EM sensor for position data. In addition to creating the 3-D anatomical map, the position module and/or the console can use the position data for graphic visualization of the catheter superimposed on the 3-D anatomical map so the location of the catheter distal tip is visually represented on the display to the operator.

In some embodiments, contact between the catheter distal tip and a surface of the heart model for the acquisition and recording of data, including position data and electrophysiological data, is determined solely by tactile sensory of the operator handling and manipulating the catheter. As such, the operator selectively activates an actuator (e.g., on the catheter control handle 16) to record the data, including position data and any electrophysiological data, for any one or more contacts between the catheter distal tip and the heart model.

In some embodiments, the simulation controller 110 and/or the console 30 relies in part or solely on the force sensor 60 to detect contact. Contact signals may be provided to the simulation controller 110 via the console 30 which is in communication with the simulation controller 110. In that regard, the console 30 may also provide to the simulation controller 110 position signals generated by the EM sensor of the catheter 14, so that the simulation controller 110 in turn may provide control and display signals to the console 30 to generate simulation ECGs for viewing on the display 11, simulation LATs for viewing on the display 27, or simulation lesion locations for viewing on the display 27.

In some embodiments, the simulation controller 110 relies in part or solely on the sensor mesh 124 to detect contact and provide contact and position signals to the simulation controller 110 which in response thereto provides contact and position data to the console 30. In some embodiments, the simulation controller refines or disambiguates the contact and position signals from the sensor mesh using video data received from the camera system 130 configured to image the 3-D heart model and the catheter. In some embodiments, the console 30 processes the contact and position data provided by the simulation controller 110 in rendering the 3-D anatomical map for display on the first display 27. In some embodiments, the console 30 processes the contact and position data in providing visual indicia of simulation lesions that are superimposed on the 3-D anatomical map.

In some embodiments where the console 30 operates in the absence of or without detection of electrophysiological data from the 3-D heart model 122, the simulator controller 110 may provide to the console 30 control and display simulation ECGs for display on the second display 11 for viewing by the operator in training the operator to familiarize and recognize ECGs, including normal ECGs and defective ECGs (arrhythmias) of the one or more chambers represented by the 3-D heart model 122. In some embodiments, the simulator controller 110 can provide signals to the sensor mesh 124 to emit simulation intracardiac ECGs for detection by the catheter 14, as the catheter 14 would detect actual intracardiac ECGs in a patient's heart.

The simulation ECGs may include, for example, ECGs representative of a normal and healthy right atrium and ECGs representative of a defective right atrium, such as a right atrium experiencing arrhythmia, e.g., atrial flutter or atrial fibrillation. Other examples, including ECGs representative of a normal and healthy right ventricle and ECGs representative of a defective right ventricle, such as a right ventricle experiencing arrhythmia, e.g., ventricular tachycardia.

In some embodiments, the simulation controller 110 provides to the console 30 control and display signals representative of simulation ECGs, for example, LATs for display on the first display 27 in rendering the anatomical map into an electroanatomical map with visual indicia of simulation electrophysiological data superimposed on the anatomical map.

In some embodiments, the system 100 operates in a "diagnostic" mode followed by a "therapeutic" mode, where in the "diagnostic mode" the operator uses the catheter to map a chamber of interest in the heart model 122 for generating a 3-D anatomical map representative of the chamber of interest of the heart model that is displayed on the first display 27, as described above. As part of the diagnostic mode, the simulator controller 110 generates a graphical simulation ECGs representative of a defective chamber on the second display 11. The display of simulation ECGs, as described above, may be implemented via the simulator controller 110 providing the console 30 control and display simulation intracardiac ECG signals for the second display 11. The display of simulation ECGs may also be implemented via the simulator controller 110 providing the console control and display simulation LATs signals for the first display 27 to be superimposed on the anatomical map in rendering an electroanatomical map. The display of simulation ECGs may further be implemented via the simulator controller 110 providing the sensor mesh with simulation intracardiac ECGs for detection by the catheter's electrodes. In any case, the operator studies the one or more simulation ECGs shown on the displays 11 and 27 and devises a therapeutic ablation procedure, including suitable ablation locations or one or more patterns of ablation in or on the heart model.

When the system is switched to or operates in a "therapeutic" mode, the operator manipulates the catheter to place distal tip 15 (and electrode 17A) in contact with one or more suitable ablation locations in the heart model 122 so that the operator can simulate activation of the RF ablation module to form lesions at the ablation locations. When contact is assessed (e.g., by tactile sensory, force sensor 60, and/or contact activation of sensor mesh 124), the position data of the contact is collected by the EM sensor, processed by the position module 55, and used by the console 30 to provide a visual indicia representative of a simulation lesion that is superimposed on the 3-D map 154 shown on the first display 27. In other embodiments, the position data of the contact may be collected by the sensor mesh 124, processed by the simulation controller 110 and provided to the console 30 to provide a visual indicia representative of a simulation lesion that is superimposed on the 3-D map 154 shown on the first display 27.

In some embodiments, for any of the embodiments of the system 100, as the operator moves the catheter distal tip from location to location in simulating sequential contact locations to form lesions, the simulation controller 110 is tracking in real-time the accumulation of position data either from the sensor mesh 124 or the position module 55 so that the simulation controller 110 can change and update the simulation ECGs to provide evolving simulation ECGs responsive to the ablation locations or ablation patterns implemented by the operator so that the operator can better experience a "live" ablation session where errant electrical impulses of a patient's heart actively react to the formation of lesions in real-time. And when the simulation controller 110 tracking the accumulation of position data has determined that the operator has formed an appropriate number of simulation lesions in the appropriate locations corresponding to the defective simulation of errant electrical activity the chamber, so as to simulate an effective "block" or "isolation" of the abnormal electrical impulses, the simulation controller 110 can change and update the simulation ECGs to provide a normal ECG in simulating an effective and successful ablation procedure. For example, the simulation that is run on the simulation controller 110 may include a state of the simulated heart that includes the locations of the lesions in the simulated heart tissue and the conduction pathways through the simulated heart. As such, the simulation ECGs generated by the simulation controller depend on the state of the simulation, such as the creation or presence of a lesion that changes the state of the simulated heart (e.g., adds lesions that may change the conduction pathways through the tissue of the simulation of the heart), that allows the simulation controller 110 to generate simulation ECGs that react to the changes caused by the simulated ablation.

As such, the user of the simulation system 100 may receive feedback from the simulation system 100 through the display device 150, such as viewing a 3D model of the endocardial anatomy as measured, displaying the current activation sequence from recorded electrograms, viewing current electrograms, viewing the current location of the electrode catheter in the heart, displaying the locations of sites of interest, such as places where simulated RF energy has already been applied, and viewing the effects of performing the simulated ablations (e.g., simulated applications of RF energy) of various portions of the simulated heart during the training procedure.

FIG. 6A is an illustration of a sensor mesh according to one embodiment of the present invention. The sensor mesh includes "horizontal" sensing lines 124A and "vertical" sensing lines 124B. The terms horizontal and vertical are used herein merely for the sake of convenience in describing the sensor mesh 124 and do not necessarily refer to any physical direction of the sensing lines 124A and 124B when placed within the heart model 122. The horizontal sensing lines 124A are substantially parallel to each other (e.g., the horizontal sensing lines 124A substantially do not cross or intersect with one another). Similarly, the vertical sensing lines 124B are substantially parallel to each other. The horizontal sensing lines 124A are arranged to cross or intersect with the vertical sensing lines 124B at crossing regions to form a sensing matrix. For example, in the embodiment shown in FIG. 6A, when the sensor mesh 124 is flattened, the horizontal sensing lines 124A are perpendicular to the vertical sensing lines 124B. An insulating sheet may be placed between the horizontal sensing lines 124A and the vertical sensing lines 124B. When force is applied to the sensor mesh along a direction perpendicular to the plane of the mesh, the sensor mesh generates a signal corresponding to the location where force is applied. This signal may correspond to one or more of the horizontal sensing lines 124A being displaced to be closer to one or more of the vertical sensing lines 124B, or vice versa.

Figure 6B:
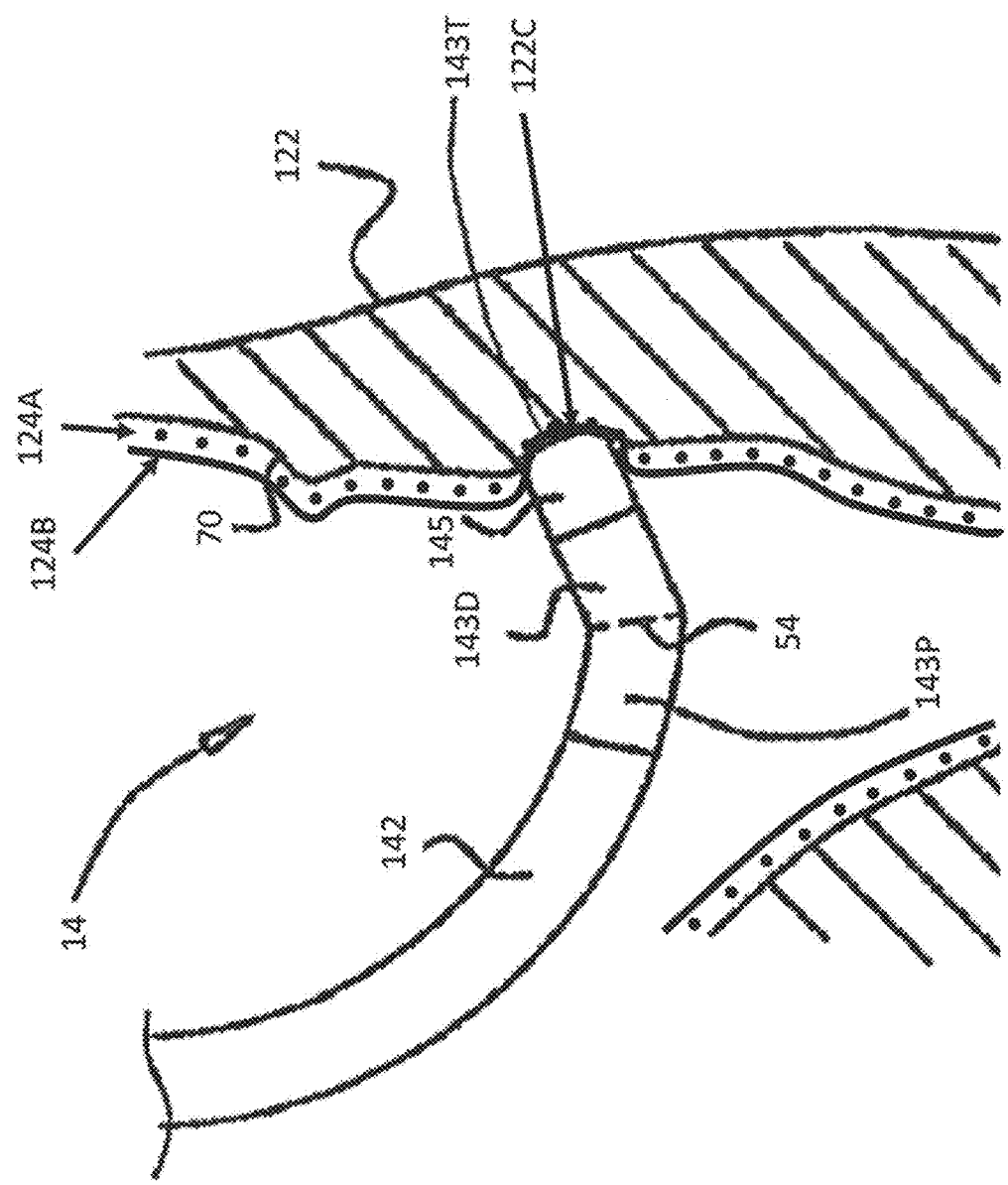
FIG. 6B is an illustration of a physical heart model with an integrated sensor mesh according to one embodiment of the present invention, in which a catheter tip has made contact with the sensor mesh.

FIG. 6B is an illustration of a physical heart model with an integrated sensor mesh according to one embodiment of the present invention, in which a catheter tip has made contact with the sensor mesh 124. The sensor mesh 124 is disposed on the inner walls of the heart model 122. The horizontal sensing lines 124A extend into and out of the plane of FIG. 6B (and are therefore depicted as dots), and one of the vertical sensing lines 124B extends along the plane of the plane of FIG. 6B. As shown in FIG. 6B, the distal section 143 of the catheter 14 includes a proximal portion 143P, a distal portion 143D, and a distal tip end 143T. The distal section 143 carries at least a tip electrode 145 on its distal tip end 143T.

FIG. 6B depicts the distal tip end 143T as making contact with a portion 122C of the inner wall of the physical heart model 122. At this point or location of contact 122C, the distal tip end 143T compresses at least one of the vertical sensing lines 124B against the inner wall of the physical heart model 122, bringing the one or more of the vertical sensing lines 124B closer to some of the horizontal sensing lines 124A.

In some embodiments of the present invention, sensing signals are sequentially supplied from the simulation controller 110 to one set of sensing lines and signals may be read from the other set of sensing lines. For example, scanning signals in the form of voltage signals (e.g., an alternating voltage signal) may be sequentially applied to the horizontal sensing lines 124A and voltages are read out through the set of vertical sensing lines 124B. The detected change in voltage on the vertical sensing lines 124B while the scanning signal is applied to one of the horizontal sensing lines 124A reflects the capacitance between the one of the horizontal sensing lines 124A and the vertical sensing lines 124B (e.g., the capacitance in the crossing region of the horizontal sensing line with the vertical sensing line).

The capacitance of a crossing region may change based on the proximity of the distal tip end 143T and the tip electrode 145. In particular, the tip electrode 145 may have a dielectric constant different from the ambient environment (e.g., liquid or air). As such, when the tip electrode 145 enters the electric field formed in a crossing region of one of the horizontal sensing lines 124A and one of the vertical sensing lines 124B, the capacitance of the crossing region changes.

The capacitance of a crossing region may also change depending on the distance between the sensing lines of the crossing region. As such, when the sensor mesh is compressed in a crossing region, the capacitance may be different (e.g., lower) than that in the relaxed, uncompressed state. This allows detection of which portions of the sensor are compressed, thereby allowing detection of which portions of the inner surface of the physical heart model 122 are in contact with the catheter. In addition, in some embodiments, an amount of force applied to the physical heart model 122 can be determined based on the magnitude of the change in capacitance (e.g., greater amounts of force may cause greater compression and therefore cause the sensing lines to be closer together than they would be under smaller amounts of force).

While the embodiment shown in FIG. 6B illustrates the sensor mesh 124 as being disposed on an interior surface of the inner walls of the physical heart model 122, embodiments of the present invention are not limited thereto. In some embodiments of the present invention, the sensor mesh is embedded within the walls of the physical heart model 122, where deformation of the shape of the wall due to contact may also cause a change in capacitance.

In some embodiments of the present invention, the sensor mesh 124 is also used to emit simulation intercardiac ECGs for detection by the catheter 14. These signals may be generated by, for example, identifying a location of contact by the catheter 14, identifying a simulation intercardiac ECG corresponding to the current state of the simulation and the location, and applying voltages corresponding to the ECG signals across the sensing lines that are in contact with the catheter 14 (in some embodiments, all of the sensing lines are be supplied with the corresponding voltages). As described in more detail below, the simulation ECG signals may be stored as sampled analog signals (e.g., an audio format), and the simulation ECG signals may be supplied to the sensor mesh in a non-overlapping frequency band than the sensing signals, thereby allowing the sensing signals and the simulation ECG signal to be supplied through the sensor mesh 124 without interfering with one another. For example, the simulation signals may be supplied within an audio frequency band (e.g., up to about 20 kHz), and the sensing signals may be applied at a higher frequency (e.g., using alternating current signals above 100 kHz).

Figure 7:
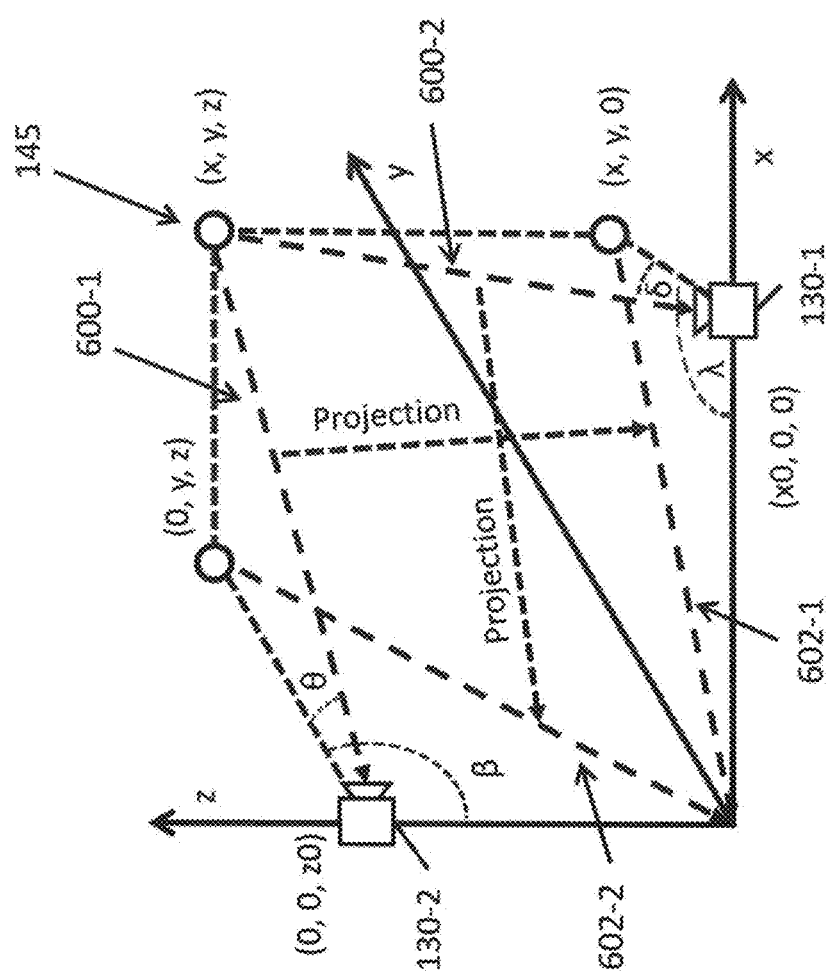
FIG. 7 is an illustration of the estimation of a location of a catheter tip using a method according to one embodiment of the present invention.

FIG. 7 is an illustration of the estimation of a location of a catheter tip using a method according to one embodiment of the present invention. While the sensor mesh 124 may be used to detect which portions of the inner surface of the heart model 122 are in contact with the catheter, multiple portions of the catheter 14 may be in contact with the sensor mesh at a given time, which may make it ambiguous as to which detected contact corresponds to the location of the distal tip end 143T (or the tip electrode 145). The location of the distal tip end 143T (or the tip electrode 145) may be relevant to the simulation for the purpose of determining which portion of the heart will be ablated when the user supplies an ablation input command (e.g., by activating a switch on the control handle 16 of the catheter 14.

Figure 3A:
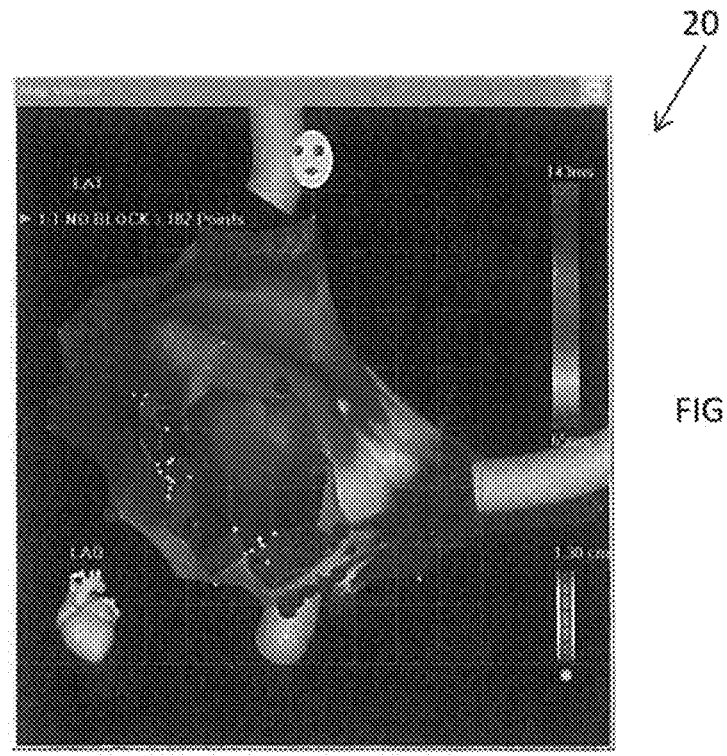
FIGS. 3A and 3B are sample 3-D representations generated by the system of FIG. 1A, showing locations of ablation and lesion formation forming a line of block.
Figure 3B:
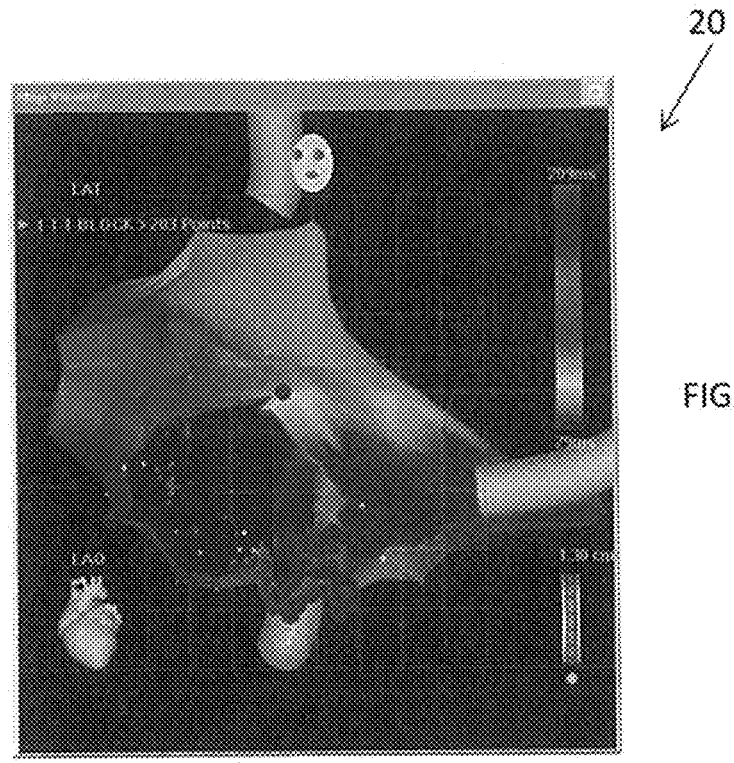

As such, in order to disambiguate between the various points of contact, in some embodiments, the cameras (or camera system) 130 are used to track the location of the catheter distal tip end 143T. As shown in FIG. 5, the cameras 130 may be located at different locations around the heart model 122 to have overlapping and different views. As one example, the cameras 130 may be located with their optical axes along perpendicular axes (e.g., the x and z axes, as shown in FIGS. 3 and 5). For example, the first camera 130-1 may be configured to captures images along the x-y plane and the second camera 130-2 may be configured to capture images along the y-z plane.

The catheter tip 145 may have a distinctive color (e.g., red) so that the cameras can more easily identify or isolate the catheter tip 145 within the images captured by the cameras of the heart model 122. As noted above, because the heart model 122 is transparent, the cameras 130 are able to image the catheter tip 145 in the interior of the heart model.

According to one embodiment of the present invention, the spatial position of the catheter tip is calculated by its direction angle and shape image from the viewpoint of the cameras 130, which are imaging known locations on the physical heart model 122 with fixed direction. The video collection and processing system 136 may be configured to analyze the images captured by the first camera 130-1 and the second camera 130-2 to determine the location (x, y, z) of the catheter tip 145. For the sake of convenience in describing the system, the first camera 130-1 is located at position (x0, 0, 0) and the second camera 130-2 is located at position (0, 0, z0). The catheter tip 145 may be located within the images captured by the first camera 130-1 and the second camera 130-2.

Based on the existing known positions of the physical heart model 122 within the images and the angles from the two cameras, the position of the catheter tip can be calculated. The location of the catheter tip can be located in the images captured by the first camera 130-1 and the second camera 130-2 based on finding pixels having the distinctive color (e.g., red) of the catheter tip. Considering the first camera 130-1, the location (x, y, z) of the catheter tip has an elevational angle δ and a transverse angle λ with respect to the optical axis of the camera. These angles δ and λ can be calculated based on the known field of view (FOV) of the first camera 130-1. For example, if it is known that the first camera 130-1 has a horizontal field (in the x direction) of view of 48° and a vertical field of view (in the y direction) of 27.0°, and an image size of 1280 pixels by 720 pixels then identifying the location of the catheter tip at pixels that are at approximately the 320th pixel along the x direction would indicates that the angle A is about 12° (48°×320 pixels/1280 pixels). A similar calculation can be performed for the angle δ based on the position of the pixels along the y direction of the image. Similar calculations can also be performed for the second camera 130-2 to determine the angles β and α. The computed angles can be used to identify rays 600-1 and 600-2 that have origins at the cameras 130-1 and 130-2, respectively. The rays 600-1 and 600-2 intersect at the location (x, y, z) of the catheter tip. Alternatively, the position y can be calculated based on the intersection of the projection of the ray 600-1 to the x-y plane, and calculating the intersection between the projected ray 602-1 and a line extending from the first camera 130-1 at angle λ. As still another option, the position y can be calculated based on the intersection of the projection of the ray 602-1 to the y-z plane, and calculating the intersection between the projected ray 602-2 and a line extending from the second camera 130-1 at angle β.

Figure 8:
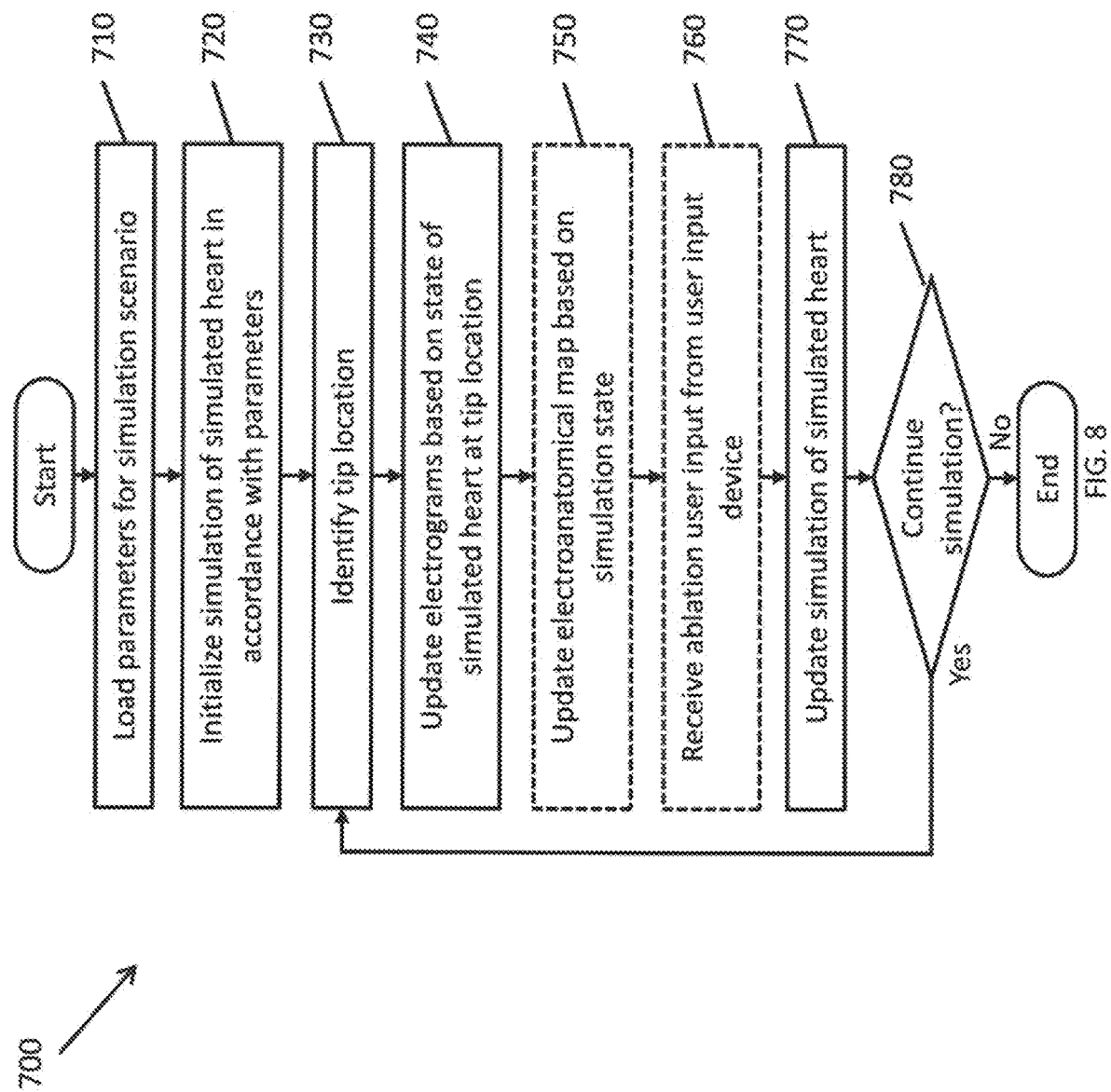
FIG. 8 is a flowchart illustrating a method for simulating a catheter ablation procedure according to one embodiment of the present invention.

FIG. 8 is a flowchart illustrating a method for simulating a catheter ablation procedure according to some embodiments of the present invention. The various operations of the method may be performed by a simulator system 100 (e.g., the simulation controller 110, including a computer system customized to simulate a heart and to simulate the effects of performing a surgical procedure on the simulated heart).

In some embodiments of the present invention, the simulation system operates in a plurality of different modes, which may correspond to different phases of a cardiac catheter-based mapping and ablation procedure. These modes may include: a mapping mode, corresponding to the initial mapping of the structure of a heart and its electrical conduction patterns; and a therapeutic mode, corresponding to a phase in which the electrical conduction patterns of the heart are measured and ablative power is applied to portions of the heart to modify the conduction patterns.

In operation 710, the simulation controller 110 may load parameters for a simulation. The parameters may define various aspects of the simulation to be performed, such as the particular type of heart to be modeled (e.g., size or shape of the heart, or child versus adult heart), the types of diseases affecting the heart, and which portions of the heart are affected by the one or more diseases (e.g., particular portions of the heart that have faulty electrical pathways), blood pressure, and the like. The parameters may also include information regarding other medical conditions of the simulated patient that may have an effect on what would be observed during a procedure (e.g., hypertension, hemophilia, etc.).

The parameters may be defined prior to the simulation session by a simulation designer. In addition multiple sets of parameters can be stored (e.g., in the simulation controller 110) as different scenarios such that the simulator can be easily configured to simulate different conditions by loading an appropriate scenario. For example, different scenarios can be used to simulate different types of cardiac arrhythmias such as atrial fibrillation, atrial flutter, supraventricular tachycardias (SVT), and Wolff-Parkinson-White syndrome in different types of patients (e.g., children versus adults) and under various conditions.

In some embodiments, the physical heart model itself may also be varied based on the simulation scenario. For example, when simulating a procedure performed on an adult versus performed on a child may involve the use of a larger or a smaller physical heart model 122, respectively.

In operation 720, the simulation controller 110 initializes a digital simulation of a heart in accordance with the loaded parameters. The simulated heart model (or virtual heart model) may be maintained within the memory of the simulation controller 110 and updated in accordance with instructions stored in the memory and executed by the processor, where the simulation simulates the electrical activity at every location of the simulated heart over time (e.g., a map of the electrical conduction velocity at each location of the heart or the intracardiac electrocardiography or ECG signals that would be measured if a catheter tip including an ECG pickup were brought into contact with that portion of a heart). The simulation controller 110 may also store information corresponding to the 3D electroanatomic map 154 of the heart to be displayed on the display device 150.

In operation 730, the simulation controller 110 identifies a tip location or point, if any. This tip location may be position corresponding to both physical coordinates within the physical heart model 122 and virtual coordinates within the three-dimensional virtual heart model, where the position is computed based on signals received from the sensor mesh 124 and the cameras 130. For example, the tip contact location may include a three-dimensional (x, y, z) coordinate identifying a particular location within the volume of the physical heart model 122 or a particular location within the three-dimensional heart model system 120. Furthermore, if the distal end 143 of the catheter 14 is in contact with the sensor mesh 124, the tip location may include a two-dimensional (x, y) coordinate identifying a particular location on the sensor mesh 124 or a particular location on the interior surface of the physical heart model 122. In some circumstances, when the distal end 143 is not in contact with the sensor mesh, no tip contact is determined.

Figure 9:
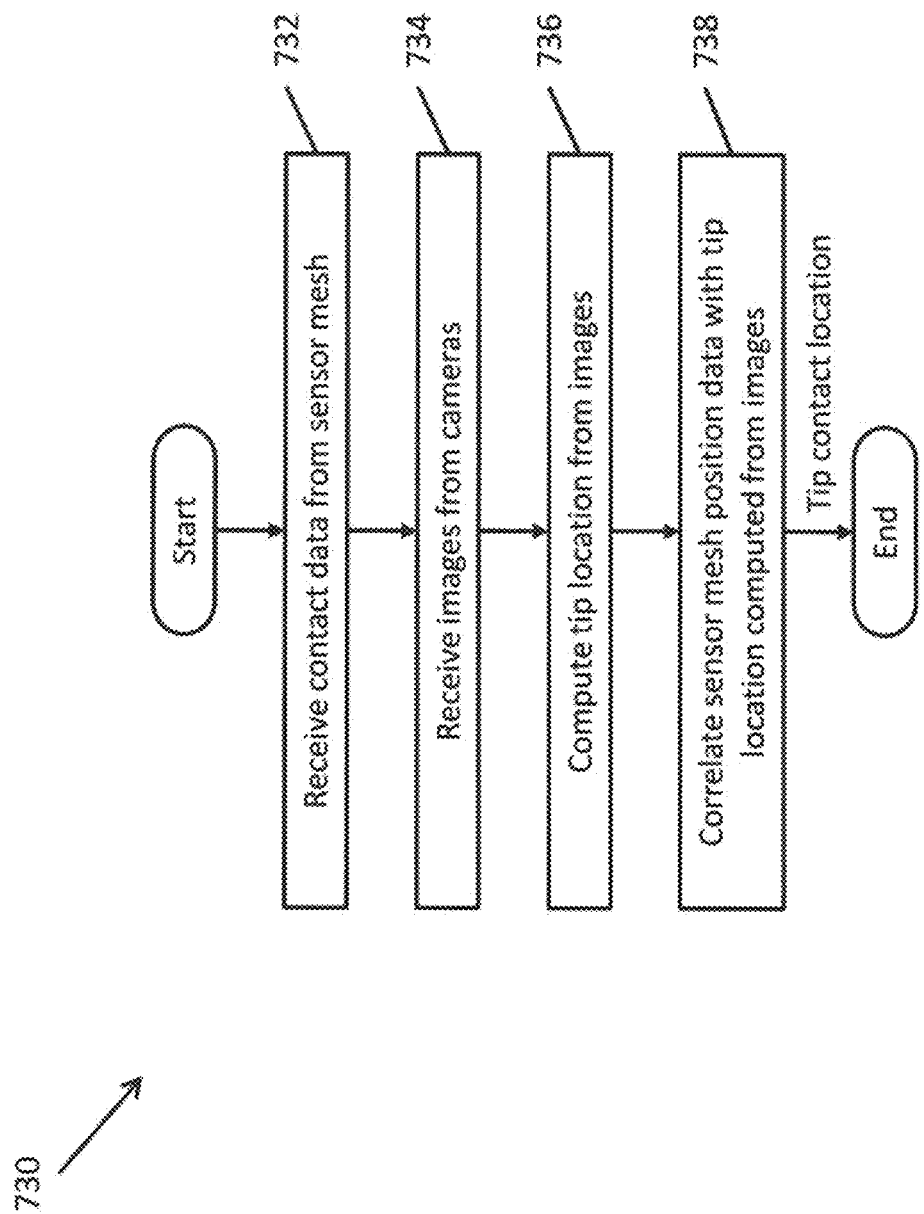
FIG. 9 is a flowchart illustrating a method for determining a tip contact location according to one embodiment of the present invention

FIG. 9 is a flowchart a method for identifying a tip contact point according to one embodiment of the present invention. In operation 732, the simulation controller 110 receives contact data from the sensor mesh 124. This may include, for example, information regarding a change in capacitance at one or more sensing regions of the sensor mesh 124. In operation 734, the simulation controller 110 receives images from the cameras 130. These images may be supplied as, for example, bitmap images (e.g., JPEG files or Portable Network Graphics or PNG files) captured by the cameras or as video (e.g., MPEG-2 or H.264/MPEG-4 video). In operation 736, the simulation controller 110 processes the images captured by the cameras 130 to compute a three-dimensional position (x, y, z) of the distal tip end 143T (or the tip electrode 145), as described above with respect to FIG. 7.

In operation 738, the simulation controller 110 correlates the sensor mesh contact data from operation 732 with the tip location calculated from the camera images in operation 736 to determine a tip location. In the case where the contact data includes multiples points of contact (e.g., the sensor mesh 124 was contacted in multiple places), this correlation may include comparing each of the multiple points of contact with the three-dimensional tip location computed from the images. The point of contact on the sensor mesh that is closest to the three-dimensional tip location can is then identified as the tip contact location. In some circumstances, parts of the distal end 143 may be in contact with portions of the sensor mesh 124 without the tip electrode 145 and/or the distal tip end 143 being in contact with the sensor mesh 124. As such, none of the points of contact received from the sensor mesh 124 may be sufficiently close to the three-dimensional tip location to identify actual tip contact. As such, in some circumstances, when the tip electrode 145 is not in contact with the sensor mesh 124, the tip location is determined solely from the images received from the cameras 130.

Returning to FIG. 8, in operation 740, the simulation controller 110 updates the electrograms 152, based on the state of the simulated heart and the tip location. For example, the simulation controller translates the tip location from real coordinates (e.g., coordinates on the physical heart model) into virtual coordinates (coordinates on the simulated heart model). In one embodiment, for each simulation scenario, the simulation controller 110 stores a plurality of different electrical physiological (EP) signals, each EP signal corresponding to a different location on the heart. The simulation controller 110 displays, on the electrograms 152, the EP signal corresponding to the detected contact position of the catheter tip on the sensor mesh 124 of the physical heart model 122. In some embodiments, the EP signals are stored in the database in a data file format appropriate for a sampled analog signal (e.g., an audio format), such as pulse-code modulation (PCM) or a compressed format such as MPEG audio layer III (MP3).

As the simulation progresses, the simulation controller 110 automatically updates the state of the simulated (or virtual) heart model with the new electrical states over the surfaces or the volume of the simulated heart. For example, during a simulation of an electroanatomical mapping process, the simulation controller 110 updates the model in accordance with the ECG signals at various parts of the heart over the course of a heartbeat or in response to a virtual pacing signal. In some embodiments, the virtual pacing signal is controlled by the operator to be supplied at a location in the virtual heart model that is specified by the operator. As such, as the operator moves the distal section 143 of the catheter 14 to various portions of the interior surface of the physical heart model 122, the simulation controller 110 identifies the electrical state of the simulated heart model at the virtual coordinates corresponding to the contact position of the distal section. For example, the simulation controller 110 may output an EP signal selected from the stored EP signals based on the current conditions of the simulation and the contact position, and the output EP signal may be displayed to show the local electrogram at the point of contact among the electrograms 152. In some embodiments, the simulation controller 110 also generates body surface pad signals based on the state of the simulation (e.g., by loading ECG signals corresponding to the various pads 38 based on the current state of the simulation).

In some embodiments in which an electrophysiology mapping and ablation system 10 is used, the system 10 may generate the anatomical map based on the position of the catheter tip, as detected by the magnetic fields, and the simulation controller 110 provides simulated signals to the system 10 such that the system 10 updates the electroanatomical map based on the simulated signals.

In other embodiments without an electrophysiology mapping and ablation system 10, the generation of the electroanatomical map may be simulated. For example, during a mapping phase, the operator moves the distal tip end 143 over the interior surface of the physical heart model 122 to construct the 3-D electroanatomical map 154 of the structure of the heart. The simulation may begin with an empty 3-D electroanatomical map 154 because the physical heart model 122 has not yet been mapped. As the operator moves the distal tip end 143 to contact portions of the interior surface of the physical heart model 122, the electroanatomical map 154 is updated to include the portions of the physical heart model 122 that have been visited by the distal tip end 14. As such, the electroanatomical map may be created in a manner that is substantially similar to the manner in which such a map would be generated during an actual electroanatomical mapping process in a procedure with a live patient.

In some embodiments, in operation 750, the simulation controller 110 also updates the display 150 in accordance with the updated state of the simulated heart model, the updated electroanatomical map, and the virtual coordinates of the distal section 143 of the catheter.

For example, in embodiments without an electrophysiology mapping and ablation system 10, the simulation controller 110 may update the display of the 3-D electroanatomical map 154 in accordance with the updated electroanatomical map on display 150, which may show a representation of the heart similar to what would be shown on an electrophysiology mapping and ablation system 10 during an actual procedure, to show the electrical state of the simulated heart at the virtual coordinates. For example, in a mapping mode, only the mapped portions of the heart model will be shown. In a therapeutic mode, after the mapping of the heart model is completed, an electrical activation map can be shown across the entire surface of the displayed electroanatomical map 154. The display 150 may also show a representation of the location and orientation of the distal section 143 of the catheter 14, including the location and orientation of the tip electrode 145, whether or not the tip electrode 145 is in contact with the interior surface of the physical heart model 122 (e.g., whether the tip electrode 145 is in contact with the sensor mesh 124).

As another example, in embodiments that are used in conjunction with an electrophysiology mapping and ablation system 10, the simulation controller 110 may provide simulated EP signals to the system 10 such that the system 10 captures and displays an electrical activation map overlaid on the electroanatomical map 154.

The simulation controller 110 may also generate various other types of displays based on the underlying simulated model of a heart. These other display may include, for example, an isochronal map, a voltage map, and a mesh map.

In operation 760, ablation user input may be received from the catheter. For example, in a "therapeutic" mode, a user of the simulation system may activate an ablation command by depressing an appropriate switch on the catheter control handle. (In a functional system, this command might cause the heating of the tip electrode 145 in order to ablate a portion of the heart tissue.) In some embodiments of the present invention, the ablation user input is accepted only when the simulation is operating in the "therapeutic" mode, for example, following the completion of a simulation of an electroanatomical mapping of the physical heart model 122. In some embodiments of the present invention, the user may also identify particular locations of the interior surface of the heart as points of interest for further exploration at a later time. These locations may recorded by the simulation controller and displayed on the electroanatomical map 154.

In operation 770, the simulation controller 110 updates the state of the simulated heart model. For example, based on the simulation scenario currently loaded into the system, the simulation of the heart may progress with the standard next stages of the particular form of tachycardia or atrial fibrillation associated with the scenario. In some circumstances, the simulation scenario may be configured to change the parameters or behavior of the heart, such as simulating a change in blood pressure or other unusual condition, based on a triggering condition (e.g., a time elapsed since the beginning of the procedure or the tip reaching a particular location of the physical heart model for the first time during the procedure).

In addition, if an ablation command was received in operation 760, and the ablation command was continually supplied when the tip electrode 145 was engaged with the physical heart model 122 with sufficient force and for a sufficient amount of time, then the simulation controller may update the simulated heart model to indicate successful ablation of the portion of the heart corresponding to the virtual coordinates of the tip location. This update to the simulated heart model may change the electrical conduction patterns within the simulated heart model, in accordance with the changes in behavior of an actual heart when a portion is ablated, or change the conduction patterns in accordance with a virtual pacing signal applied to a particular portion of the simulated heart model, as controlled by the operator.

In operation 780, the simulation controller 110 determines whether the simulation is to continue. For example, the simulation may end if a "quit" or "stop" command is supplied by a user. If the simulation controller determines that the simulation is to continue, the flow returns to operation 730 to identify the current location of the catheter tip 145. In various embodiments of the present invention, the loop of operations 730 to 780 occurs at a sufficiently high frequency to provide the user with feedback that is representative of the response time of the actual system. For example, the loop may occur at a rate of 30 Hz to 60 Hz (e.g., the tip location is determined and the display is updated 30 to 60 times every second).

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

For example, while embodiments of the present invention are described herein with respect to electrophysiology and catheter ablation of heart tissue, embodiments of the present invention are not limited there to and may be extended to other applications such as providing simulators for surgical and orthopedic procedures. For example, the physical heart model 122 may be replaced with a physical model of another internal organ, and the simulated model may be replaced with a simulation of the corresponding organ, where the type of information displayed to the user of the simulator mimics the type of information seen by a health care professional during an actual procedure on a patient. It is understood that the term "anatomical map" as used herein it not necessary devoid of superimposed visual indicia or imagery corresponding to electrophysiological data.

What is claimed is:

1. A system for simulating a medical procedure comprising:
   a physical model of an organ comprising a sensor mesh, the sensor mesh being configured to generate a signal corresponding to a location where force is applied to the sensor mesh;
   a user input device comprising a distal end inserted within the physical model of the organ;
   a display device; and
   a simulation controller coupled to the sensor mesh, the user input device, and the display device, the simulation controller comprising a processor and memory, the memory storing instructions that, when executed by the processor, cause the processor to:
   initialize a simulation of the organ;
   display, on the display device, a representation of a state of the simulation of the organ;
   receive contact data from the sensor mesh, the contact data comprising a signal generated by the sensor mesh in response to force applied to the sensor mesh;
   compute a location of the distal end of the user input device on an interior surface within the physical model of the organ in accordance with the contact data;
   update the state of the simulation of the organ;
   generate a simulation output comprising a simulated electrical physiological (EP) signal, wherein the simulated EP signal is computed based on the state of the simulation of the organ and the location of the distal end of the user input device computed in accordance with the contact data from the sensor mesh;
   provide, to the display device, the simulation output comprising the simulated EP signal computed based on the location of the distal end of the user input device; and
   display, on the display device, the simulation output comprising the simulated EP signal.

2. The system of claim 1, wherein the organ is a heart.

3. The system of claim 2, wherein the simulation output comprises an electroanatomical map of the heart.

4. The system of claim 2, wherein the simulation output comprises one or more electrograms.

5. The system of claim 4, wherein the memory further stores a plurality of electrical physiological (EP) signals, each EP signal corresponding to a different location of the heart,
   wherein the instructions configured to cause the processor to update the state of the simulation comprise instructions that, when executed by the processor, cause the processor to identify the simulated EP signal corresponding to the computed location of the distal end of the user input device from the plurality of EP signals, the one or more electrograms comprising the simulated EP signal.

6. The system of claim 2, wherein the instructions configured to cause the processor to initialize the simulation comprise instructions that, when executed by the processor, cause the processor to load a scenario of a plurality of scenarios, each scenario corresponding to a different form of cardiac arrhythmia.

7. The system of claim 6, wherein the scenarios comprise scenarios corresponding to forms of cardiac arrhythmias, the forms of cardiac arrhythmias comprising:
   atrial fibrillation;
   atrial flutter;
   supraventricular tachycardia; and
   Wolf-Parkinson-White syndrome.

8. The system of claim 1, further comprising an electroanatomical mapping system coupled to the simulation controller, the electroanatomical mapping system being configured to generate an anatomical map of the model of the organ.

9. The system of claim 1, further comprising a camera system,
   wherein the memory further stores instructions that cause the processor to receive images from the camera system, and
   wherein the instructions to compute the location of the distal end of the user input device further comprise instructions to calculate the location of the distal end in accordance with images of the distal end in the received images.

10. The system of claim 9, wherein the camera system comprises a first camera and a second camera, and
    wherein the instructions configured to cause the processor to compute the location of the distal end of the user input device comprise instructions that, when executed by the processor, cause the processor to:
    compute a first elevational angle and a first transverse angle of a first ray between the first camera and the distal end of the user input device with respect to an optical axis of the first camera;
    compute a second elevational angle and a second transverse angle of a second ray between the second camera and the distal end of the user input device with respect to an optical axis of the second camera; and
    compute an intersection between the first ray and the second ray, the intersection corresponding to the location of the distal end of the user input device.

11. The system of claim 1, wherein the organ is a heart,
    wherein the memory further stores a plurality of electrical physiological (EP) signals, each EP signal corresponding to a combination of a location of the heart and a state of the heart of a plurality of states,
    wherein the instructions configured to cause the processor to update the state of the simulation comprise instructions that, when executed by the processor, cause the processor to identify the simulated EP signal corresponding to the computed location of the distal end of the user input device from the plurality of EP signals and a current state of the heart, the simulation output comprising the simulated EP signal.

12. The system of claim 11, wherein the memory further stores instructions that, when executed by the processor, cause the processor to receive user input from the user input device, and
  wherein the instructions configured to cause the processor to update the state of the simulation comprise instructions that, when executed by the processor, cause the processor to update the state based on the user input.

13. The system of claim 12, wherein the user input corresponds to applying ablative power to the heart, and
  wherein the state of the simulation is updated to indicate ablation of tissue in the simulation of the organ at the location of the distal end of the user input device in the physical model of the organ.

14. The system of claim 1, wherein the sensor mesh comprises:
  a plurality of first sensing lines substantially parallel to each other; and
  a plurality of second sensing lines substantially parallel to each other, the plurality of second sensing lines crossing the plurality of first sensing lines at a plurality of crossing regions to form a sensing matrix, and
  wherein the location of the distal end of the user input device is computed based on the contact data, the contact data being computed based on a change in an electric field between one of the first sensing lines and one of the second sensing lines.

15. The system of claim 1, wherein the physical model of the organ is configured to be devoid of electrophysiological signals emitted from the sensor mesh during operation when the distal end of the user input device is in contact with the interior surface within the physical model of the organ.

16. The system of claim 1, wherein the system is configured to generate the simulation output comprising the simulated EP signal without detection of electrophysiological data from the sensor mesh of the physical model of the organ.

17. The system of claim 1, wherein the simulation output is generated without the detection, by the distal end of the user input device, of electrophysiological data from the sensor mesh of the physical model.

18. The system of claim 1, wherein the location of the distal end comprises a two-dimensional coordinate identifying a particular location on the interior surface of the organ.

19. The system of claim 1, wherein the memory further stores instructions that, when executed by the processor, cause the processor of the simulator controller to generate the simulation output by:
  translating the location of the distal end to a plurality of virtual coordinates in a simulated model of the organ;
  identifying an electrical state of the simulated model of the organ;
  select an EP signal from a plurality of stored EP signals based on the electrical state of the simulated model of the organ and the virtual coordinates; and
  outputting the selected EP signal as the simulated EP signal of the simulation output.

* * * * *